(12) United States Patent
Billings et al.

(10) Patent No.: US 6,766,191 B1
(45) Date of Patent: Jul. 20, 2004

(54) SYSTEM AND METHOD FOR IN-VIVO HEMATOCRIT MEASUREMENT USING IMPEDANCE AND PRESSURE PLETHYSMOGRAPHY

(75) Inventors: Robert Gail Billings, Salt Lake City, UT (US); Justin S. Clark, Salt Lake City, UT (US); Jon Neese, Holladay, UT (US)

(73) Assignee: Microcor, Inc., Salt Lake City, UT (US)

( * ) Notice: Subject to any disclaimer, the term of this patent is extended or adjusted under 35 U.S.C. 154(b) by 0 days.

(21) Appl. No.: 09/571,459

(22) Filed: May 16, 2000

Related U.S. Application Data

(63) Continuation-in-part of application No. 09/121,000, filed on Jul. 23, 1998, which is a continuation-in-part of application No. 08/885,747, filed on Jun. 30, 1997, now abandoned, which is a continuation of application No. 08/602,700, filed on Feb. 16, 1996, now Pat. No. 5,642,734, which is a continuation-in-part of application No. 08/425,404, filed on Apr. 20, 1995, now Pat. No. 5,526,808, which is a continuation of application No. 08/298,795, filed on Aug. 31, 1994, now abandoned, which is a continuation of application No. 08/114,131, filed on Aug. 30, 1993, now abandoned, which is a continuation of application No. 07/592,851, filed on Oct. 4, 1990, now abandoned.
(60) Provisional application No. 60/057,166, filed on Aug. 28, 1997.

(51) Int. Cl.[7] ................................................. A61B 5/00
(52) U.S. Cl. ....................... 600/547; 600/365; 600/384; 600/390
(58) Field of Search ................................. 600/372, 382, 600/384, 386, 391–393, 481, 485, 490–492, 499–500, 504, 506, 385

(56) References Cited

U.S. PATENT DOCUMENTS

| | | | |
|---|---|---|---|
| 4,204,545 A | * | 5/1980 | Yamakoshi ................. 600/506 |
| 4,250,894 A | * | 2/1981 | Frei et al. ................ 600/382 X |
| 4,676,253 A | * | 6/1987 | Newman et al. ............. 600/506 |
| 5,111,817 A | | 5/1992 | Clark et al. |
| 5,119,823 A | * | 6/1992 | Teramoto et al. ............ 600/499 |
| 5,203,344 A | * | 4/1993 | Scheltinga et al. .......... 600/547 |
| 5,277,181 A | | 1/1994 | Mendelson et al. |
| 5,343,867 A | * | 9/1994 | Shankar ....................... 600/481 |

(List continued on next page.)

FOREIGN PATENT DOCUMENTS

| | | |
|---|---|---|
| EP | 0 417 796 A2 | 3/1991 |
| WO | WO 96/32883 | 10/1996 |

OTHER PUBLICATIONS

International Search Report dated Oct. 24, 2001.

*Primary Examiner*—Robert L. Nasser
(74) *Attorney, Agent, or Firm*—TraskBritt

(57) ABSTRACT

The hematocrit of blood (i.e., the percentage of whole blood volume occupied by red blood cells) perfusing a finger is determined by stimulating the finger with two current frequencies, one relatively high (e.g., 10 MHZ) and the other relatively low (e.g., 100 KHz). Voltages induced in the finger in response to the two current frequencies are then captured and separated into baseline and pulsatile components. The hematocrit is determined as a function of the ratio of the high frequency pulsatile component to the low frequency pulsatile component, multiplied by the ratio of the square of the low frequency baseline component to the square of the high frequency baseline component. The volume of blood perfusing the body part at which hematocrit is to be measured may be increased on each pulse by the application of external pressure to the finger, such as by applying a pressure cuff to the finger. Assemblages including two pairs of electrodes are used to effect the determination of hematocrit. The assemblages may also include a component for applying pressure to the body part at which hematocrit is measured.

24 Claims, 12 Drawing Sheets

U.S. PATENT DOCUMENTS

| | | |
|---|---|---|
| 5,499,627 A | 3/1996 | Steuer et al. |
| 5,526,808 A | 6/1996 | Kaminsky |
| 5,642,734 A * | 7/1997 | Ruben et al. |
| 5,752,512 A * | 5/1998 | Gozani .................. 600/382 X |
| 5,800,350 A * | 9/1998 | Coppleson et al. ..... 600/373 X |
| 5,803,908 A | 9/1998 | Steuer et al. |
| 5,833,602 A | 11/1998 | Osemwota |
| 5,978,691 A | 11/1999 | Mills |
| 6,128,518 A | 10/2000 | Billings et al. |

* cited by examiner

SYSTEM AND METHOD FOR IN-VIVO HEMATOCRIT MEASUREMENT USING IMPEDANCE AND PRESSURE PLETHYSMOGRAPHY

This application claims the benefit of a U.S. Provisional Application filed Aug. 28, 1997, entitled "Device and Method for In-Vivo Hematocrit Measurement Using Impedance and Pressure Plethysmography," having application Ser. No. 60/057,166, now pending, and is also a continuation-in-part of U.S. patent application Ser. No. 09/121,000, filed Jul. 23, 1998, pending, which is a continuation-in-part of U.S. patent application Ser. No. 08/885,747, filed Jun. 30, 1997, abandoned, which is a continuation of U.S. patent application Ser. No. 08/602,700, filed Feb. 16, 1996, now U.S. Pat. No. 5,642,734, which is a continuation-in-part of a patent application filed Apr. 20, 1995, having Ser. No. 08/425,404, now U.S. Pat. No. 5,526,808, which is a continuation of U.S. patent application Ser. No. 08/298,795, filed Aug. 31, 1994, abandoned, which is a continuation of U.S. patent application Ser. No. 08/114,131, filed Aug. 30, 1993, abandoned, which is a continuation of U.S. patent application Ser. No. 07/592,851, filed Oct. 4, 1990, abandoned.

BACKGROUND OF THE INVENTION

1. Field of the Invention

This invention relates generally to devices and methods for noninvasive in vivo measurement of blood hematocrit and, more specifically, to devices and methods for such measurement that use impedance and pressure plethysmography.

2. Background of Related Art

The "hematocrit" of blood, which is defined as the percentage of whole blood volume occupied by erythrocytes (i.e., red blood cells), is an important measure of patient well being in cases of trauma, blood loss by disease, iron depletion in pregnancy, dietary iron deficiency, and a number of more specific medical conditions.

Hematocrit has traditionally been measured by centrifuging a column of blood, which has been extracted from the patient, in a glass tube, until the erythrocytes are compacted by centrifugal force to one end of the tube. The hematocrit is determined by measuring the length of the tube containing dark red material and dividing by the total length of the liquid column in the tube. These length observations are usually made visually, but are also made, in some cases, by automated optical means of various designs. Besides centrifugal hematocrit determinations, hematocrit is also derived and reported by various automated blood analyzers which count erythrocytes optically in unpacked blood. This erythrocyte count correlates with packed cell hematocrit and the derived hematocrit is reported.

It is noted that the above-described methods for obtaining hematocrit are invasive, that is they require that blood be removed from the patient in order to determine the hematocrit. A non-invasive method would be desirable because it would subject the patient to less pain and inconvenience and would preserve the patient's blood for its normal functions.

It has long been recognized by biomedical researchers that the electrical impedance of blood varies with hematocrit and that, as a result of this relationship, it should be possible to derive hematocrit from the measurement of blood impedance. Hematocrit has been successfully determined by measuring the impedance of blood that has been extracted from the patient and placed in an impedance measuring cell of controlled dimensions, where a fixed volume of the blood is contained, maintained at a known temperature, and agitated to maintain uniform cell distribution. Examples of such successful measurements are given by Okada and Schwan in "An Electrical Method to Determine Hematocrits," IRE Transactions in Medical Electronics, ME-7:188-192 (1960) and by deVries et al. in "Implications of the Dielectrical Behavior of Human Blood for Continuous Online Measurement of Hematocrit," Medical & Biological Engineering and Computing, pages 445–448 (1993) (hereinafter "deVries"). Like the centrifugal methods, these methods are invasive, however, and thus do not satisfy the need for a non-invasive hematocrit measurement. The impedance methods have, however, provided the inspiration for some ingenious inventions to measure hematocrit in-vivo and non-invasively.

The first in-vivo impedance measurement of hematocrit known to the inventors was reported by Yamakoshi et al. in "Noninvasive Measurement of Hematocrit by Electrical Admittance Plethysmography Technique," IEEE Transactions, BMB-27, 3:156-161(1980). This measurement was made by immersing the finger of the test subject in a saline solution contained in a chamber fitted with impedance measuring electrodes. The electrolyte concentration of the saline solution was then varied by mixing in either water or more concentrated saline until the pulsatile variations of impedance caused by the increased volume of blood on each pulse were minimized. When this minimization of pulses occurred, the saline solution had the same resistivity as the blood in the pulsing arteries and this resistivity could be correlated against the known, previously determined relationship between resistivity and hematocrit.

U.S. Pat. No. 5,526,808 (hereinafter "the '808 Patent"), issued to Kaminsky and assigned to Microcor, Inc., the assignee of the present invention, describes another impedance method for measuring hematocrit noninvasively and in vivo. This method draws upon the observation that hematocrit determines the frequency vs. impedance profile of blood. In addition, the method of the '808 Patent uses the pulsatile change of impedance in a finger or other limb of the body that occurs when each heartbeat pushes new blood into the organ where the measurement is made to separate the non-blood tissue impedance from the blood impedance.

The mathematical model upon which this method is based relies upon the assumption that, as blood pulses into a finger or other body part where the hematocrit measurement is being made, the admittance (i.e., the reciprocal of impedance) change that occurs is due to the increased volume of blood providing a new current path in parallel with the old current path present before the pulse occurs. Thus, the difference in admittance between baseline, when no new blood is in the limb, and during the pulse, when new arterial blood has entered the limb, is due to the new blood. The numerical value of this admittance difference is proportional to the volume of the new blood times the admittance of the new blood.

As shown in deVries, the admittance vs. frequency characteristics of blood have a characteristic shape that depends upon hematocrit. Comparing the shapes of either the magnitude or the phase versus the frequency of the admittance, derived for the pulsed blood, against known characteristic hematocrit-dependent shapes gives a measure of hematocrit. The known characteristic shapes can be derived from a database obtained from patients having hematocrits independently measured by the centrifugal method previously described.

U.S. Pat. No. 5,642,734 (hereinafter "the '734 Patent"), issued to Ruben et al. and assigned to Microcor, Inc., the assignee of the present invention, describes some additional methods to obtain in vivo hematocrit results. First, the '734 Patent describes using pressurized cuffs, in various ways, to change the amount of blood in the organ (e.g., the finger) at which hematocrit is noninvasively measured. Second, the '734 Patent describes a unique electronic system for driving electrodes attached to the body part under measurement and for deriving phase, as well as amplitude information from impedance measurements of the body part. Third, the '734 Patent teaches the use of a neural network computer algorithm to relate measured impedance and other data to hematocrit based upon matching a database obtained from a number of prior measurements of patients with separately-determined hematocrits.

In the field of blood oxygen saturation measurement, as opposed to the field of blood hematocrit measurement that has been under discussion thus far, U.S. Pat. No. 5,111,817 (hereinafter "the '817 Patent"), issued to Clark et al., observes that the accurate measurement of blood oxygen saturation levels in arteries ($S_aO_2$) in a body part under measurement, such as a finger, is typically hindered by different blood oxygen saturation levels in capillaries ($S_cO_2$) in the body part. The '817 Patent teaches a method for correcting measurements of $S_aO_2$ for the effects of $S_cO_2$. In this method, a pressure cuff applies a pressure to the body part under measurement that is equal to the mean arterial blood pressure in the body part. As a result, measurements from the body part are dominated by the effects of the actual $S_aO_2$ in the body part, so that the measured $S_aO_2$ is closer to actual $S_aO_2$.

While the use of pressure cuffs are known in the art to assist in the noninvasive measurement of hematocrit and blood oxygen saturation, as is the use of electrode pairs to noninvasively measure hematocrit, the art does not teach specific configurations of apparatus that are used in the noninvasive measurement of hematocrit.

SUMMARY OF THE INVENTION

The present invention includes apparatus configured for use in the noninvasive measurement of the hematocrit of a patient. Apparatus incorporating teachings of the present invention include two or more pairs of electrodes. A pressurization component may also be associated with the apparatus of the present invention.

A first embodiment of electrodes incorporating teachings of the present invention includes four individual electrodes that are paired in inner and outer sets. The electrodes may be substantially L-shaped. A first member of each electrode is configured to contact and to be at least partially wrapped around a body part at which hematocrit is to be noninvasively measured. A second member of each electrode is configured to communicate with external electrical componentry that will either apply a voltage to the body part or measure impedance at the body part, as will be described hereinafter in greater detail. In a variation of the first embodiment, one or more of the electrodes may be substantially linear, with a first end thereof configured to be at least partially wrapped around a body part and a second end thereof configured to be connected to external electronic componentry.

A second embodiment of electrodes useful in apparatus of the present invention has two elements, each including a pliable substrate and two electrodes, an electrode of an outer set and an electrode of an inner set. The pliable substrate preferably conforms to the shape of the body part at which hematocrit is to be noninvasively measured and may include a substantially planar member or be configured to at least partially receive the body part (e.g., an open- or close-ended tube configured to at least partially receive a finger). Again, the electrodes may be substantially L-shaped and include a first member and a second member. At least a portion of the first member of each electrode is secured to and carried by the pliable substrate. Thus, as the first members of each of the L-shaped electrodes are brought into contact with a body part at which hematocrit is to be noninvasively measured and the pliable substrate of each of the two elements is at least partially wrapped around the body part, the first member of each electrode is also at least partially wrapped around the body part. In a variation of the second embodiment, one or more of the electrodes may be substantially linear, with a first end thereof configured to be at least partially wrapped around a body part and a second end thereof configured to be connected to external electronic componentry.

A third embodiment of electrodes includes a single, pliable substrate that at least partially carries four electrodes arranged relative to the substrate in inner and outer sets. The pliable substrate preferably conforms to the shape of the body part at which hematocrit is to be noninvasively measured and may include a substantially planar member or be configured to at least partially receive the body part (e.g., as an open-ended or close-ended tube configured to at least partially receive a finger). The electrodes may be L-shaped, as described previously herein with respect to the first and second electrode embodiments, or substantially linear, and are configured to communicate with external electronic componentry.

Apparatus incorporating teachings of the present invention also include a pressurization component configured to apply a predetermined amount of pressure to the body part at which hematocrit is to be noninvasively measured.

A first embodiment of the pressurization component includes a pliable bladder configured to be at least partially wrapped around the body part, over the inner and outer pairs of electrodes, so as to apply increased pressure to the body part as pressure within the bladder is increased (e.g., with air or another fluid).

In a second embodiment, a pliable substrate upon which portions of the electrodes are carried, as in the second and third electrode embodiments described previously herein, comprises a pliable bladder. Accordingly, at least a portion of at least one electrode of each of the inner and outer electrode pairs may be secured to or otherwise carried by the pliable bladder. Prior to introducing pressure into the pliable bladder, the bladder may be substantially planar or configured to at least partially receive the body part at which hematocrit is to be noninvasively measured (e.g., as an open-ended or close-ended tube configured to at least partially receive a finger).

These pliable bladder embodiments of the pressurization component are configured to be connected to a source of pressure. As the pliable bladder is pressurized (e.g., by air pressure or pressure of another fluid), pressure is applied to at least a portion of the body part.

In addition, these pliable bladders may line a receptacle formed in a rigid member and configured to at least partially receive the body part.

In a third embodiment of pressurization component incorporating teachings of the present invention, inner and outer pairs of electrodes, such as those of the first, second, and third electrode embodiments described previously herein, are placed in contact with and at least partially wrapped around a body part at which hematocrit will be measured.

The body part is at least partially inserted into a pressure chamber, which is in fluid communication with a source of positive pressure. Portions of one or both electrodes of the inner and outer pairs of electrodes in contact with the body part may also be inserted into the pressure chamber. As the body part is positioned within the pressure chamber, an at least partial seal is formed around the body part. Accordingly, as a positive pressure forms within the pressure chamber, pressure will be applied to the body part.

A system for noninvasively measuring the hematocrit of blood perfusing a living body part (e.g., a finger) in accordance with teachings of the present invention includes a non-invasive hematocrit measurement apparatus and external electronic componentry associated therewith. The electronic componentry of the system includes circuitry that drives first and second alternating currents of different frequencies (e.g., 100 KHz and 10 MHz) between separate points on the body part. The alternating currents may be applied to the body part through input electrodes attached to the body part at the separate points. Also, additional circuitry monitors first and second signals (e.g., voltage waveforms) induced in the body part by the first and second currents (e.g., by monitoring output electrodes attached to the body part), and other circuitry generates first and second pulsatile signals and first and second baseline signals from the first and second induced signals. Determining circuitry then calculates the hematocrit of the blood from the first and second pulsatile signals and the first and second baseline signals. This calculation may be performed, for example, by determining the hematocrit (H) from the following equation:

$$[(1+(f-1)H)/(1-H)]\{1+[((af(e^{-bx}-c))x/(1-x))-1]H\}/\{1+[((af(e^{-bx}-c))/(1-x))-1]H\}=C\cdot(\Delta\text{Volt}_H/V_H^2)/(\Delta\text{Volt}_L/\text{Volt}_L^2),$$

where (f, a, b, x, c, and C) are various constants, as will be described below, $\Delta\text{Volt}_H$ and $\Delta\text{Volt}_L$ are the first and second pulsatile signals, and $V_H$ and $V_L$ are the first and second baseline signals.

In accordance with another embodiment of the system of the present invention, a system for measuring the hematocrit of blood perfusing a living body part includes electrodes positioned on the surface of the body part. A measuring device measures the electrical impedance at one or more frequencies between the electrodes. Also, a chamber is positioned to surround the body part between the electrodes, and a measuring apparatus measures pulsatile blood volume by the pulsatile-related change in internal pressure within the chamber. Further, a calculating device (e.g., a programmed microprocessor) determines the blood hematocrit from the measurements of impedance and pulsatile blood volume. The device may determine the hematocrit H in accordance with the following equations:

$$H=(\rho-58)/(0.01\ \rho+0.435), \text{ and}$$

$$\rho=\Delta V Z_0^2/L^2\Delta Z,$$

where $\Delta V$ is the change in pulsatile blood volume at any point in time, $\Delta Z$ is the change of impedance at the same point in time, L is a constant which will be described below, and $Z_0$ is the baseline impedance at the beginning of each pulse.

In a further embodiment, the system for determining blood hematocrit includes circuitry that produces a current signal including a first, relatively low frequency portion and a second, relatively high frequency portion, and the hematocrit measuring apparatus, which stimulates a living body part containing blood with the current signal. Also, additional circuitry of the hematocrit measuring apparatus is used to sense voltages at the first and second frequencies induced in the body part by the stimulation thereof, and further circuitry detects signal envelopes of the sensed voltages, with each signal envelope having a pulsatile component and a baseline component. Isolation circuitry isolates the pulsatile components and baseline components of the detected signal envelopes, and extraction circuitry extracts one or more sets of time-matched segments of the isolated pulsatile components and one or more sets of time-matched segments of the isolated baseline components. Further, other circuitry effectively correlates the blood hematocrit to the product of the ratio of the time-matched segments of the pulsatile components and the inverse ratio of the squares of the time-matched segments of the baseline components.

Another embodiment of the system includes an apparatus for determining the hematocrit of blood perfusing a living body part from relatively low frequency pulsatile and baseline signals induced in the body part, and from relatively high frequency pulsatile and baseline signals also induced in the body part, includes circuitry that effectively determines the ratio of the product of the relatively high frequency pulsatile signal and the square of the relatively low frequency baseline signal to the product of the relatively low frequency pulsatile signal and the square of the relatively high frequency baseline signal. The apparatus also includes circuitry that correlates the blood hematocrit to the effectively determined ratio.

Other embodiments of the invention include methods of measuring the hematocrit of blood perfusing a living body part, and a method of determining blood hematocrit, that generally correspond to the systems and apparatus described above.

Other features and advantages of the present invention will become apparent to those of skill in the art through a consideration of the ensuing description, the accompanying drawings, and the appended claims.

DETAILED DESCRIPTION OF THE PREFERRED EMBODIMENTS

The disclosures of U.S. Pat. No. 5,111,817, issued to Clark et al.; U.S. Pat. No. 5,526,808, issued to Kaminsky; and U.S. Pat. No. 5,642,734, issued to Ruben et al., are hereby incorporated in their entireties by this reference.

Figure 1:
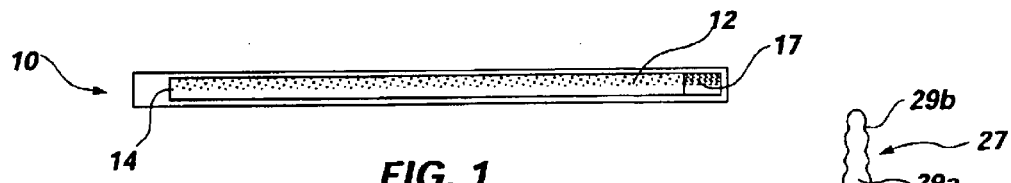
FIG. 1 is a top view of a substantially linear electrode useful in apparatus according to the present invention.

Apparatus Securable to a Body Part to Effect a Noninvasive Measurement of Hematocrit FIG. 1 illustrates a first embodiment of an electrode 10 that is useful in effecting the method of the present invention. Electrode 10 is formed from a conductive material, such as a thin metal or metal-lined sheet, and includes a first end 12 and an opposite, second end 14. First end 12 is configured to contact and, preferably, to be at least partially wrapped around a body part, such as a finger, at which hematocrit is to be measured in accordance with teachings of the present invention. Second end 14 is configured to be connected to external electronic componentry (not shown) that effects the hematocrit measurement. First end 12 may include a retention component 17 thereon, depicted as being quantity of pressure sensitive adhesive, so as to hold electrode 10 in contact with or around a body part. The pressure sensitive adhesive of retention component 17 is preferably an electrically conductive adhesive that secures electrode 10 directly to the body part. Exemplary conductive adhesives include that sold under the trade name HYDROGEL® from a number of suppliers, such as Avery Dennison, Specialty Tape Division, of Painesville, Ohio, and that sold as AQUA-TRIX™ II by Hydromer, Inc. of Somerville, N.J. Although adhesive retention component 17 is illustrated as covering substantially all of electrode 10, an adhesive retention component 17 may alternatively cover a much smaller region of electrode 10 that will adequately secure electrode 10 into contact with the body part. For example, the adhesive of retention component 17 may be disposed between electrode 10 and the body part, or retention component may be configured and located to adhere to another portion of electrode 10 and to secure the same at least partially around the body part.

Figure 1A:
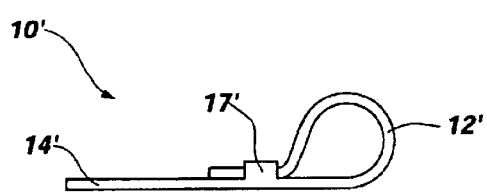
FIG. 1A is a variation of the substantially linear electrode shown in FIG. 1.

A variation of a substantially linear electrode 10' is shown in FIG. 1A. Electrode 10' includes a retention component 17', in this case a sleeve, located between a first end 12' and a second end 14' of electrode 10'. As depicted, retention component 17' is configured to receive and retain first end 12' of electrode 10' as first end 12' is looped around a body part at which hematocrit is to be measured. By pulling second end 14' taut through retention component 17', electrode 10' may be snugly secured to the body part.

Figure 2:
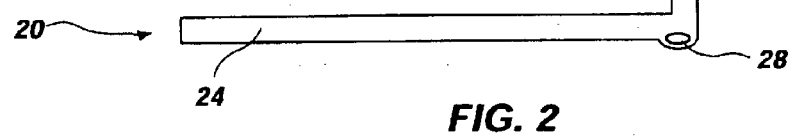
FIG. 2 is a top view of a variation of the electrode shown in FIG. 1, wherein the electrode is configured with an L-shape.

Another embodiment of an electrode 20 that may be used in the present invention is illustrated in FIG. 2. Electrode 20 is substantially L-shaped and includes a first member 22 and a second member 24. Electrode 20 is formed from a conductive material, such as a thin metal sheet or a metal-lined sheet. First member 22 of electrode 20 is configured to contact and, preferably, to be at least partially wrapped around a body part, such as a finger, at which hematocrit is to be measured in accordance with the method of the present invention. FIG. 2 illustrates electrode 20 as including an exemplary retention component 27, which, as illustrated, includes a receptacle 28 at the junction between first member 22 and second member 24. Receptacle 28 is configured to receive an end portion 29 of first member 22 as first member 22 is looped around a body part at which hematocrit is to be measured. As shown in FIG. 2, end portion 29 is configured with a series of retaining regions 29a, adjacent regions having therebetween constricted regions 29b of lesser widths. Retaining regions 29a are wider than the width of receptacle 28, while the widths of constricted regions 29b are about the same or less than the width of receptacle 28. Thus, as end portion 29 is inserted into receptacle 28, a retaining region 29a that has been pulled through receptacle 28 secures end portion 29 within receptacle 28 to interconnect receptacle 28 and end portion 29. In this manner, receptacle 28 and end portion 29 interlock to securing first member 22 in place around a body part. Second member 24 of electrode 20 is configured to be connected to external electronic equipment that effects the method of the present invention.

Alternatively, electrodes 10 or 20 may be formed from a deformable material that substantially sets upon deformation so as to retain a portion of electrode 10, 20 in contact with and secure that portion of electrode 10, 20 to the body part at which hematocrit is to be measured.

Figure 3:
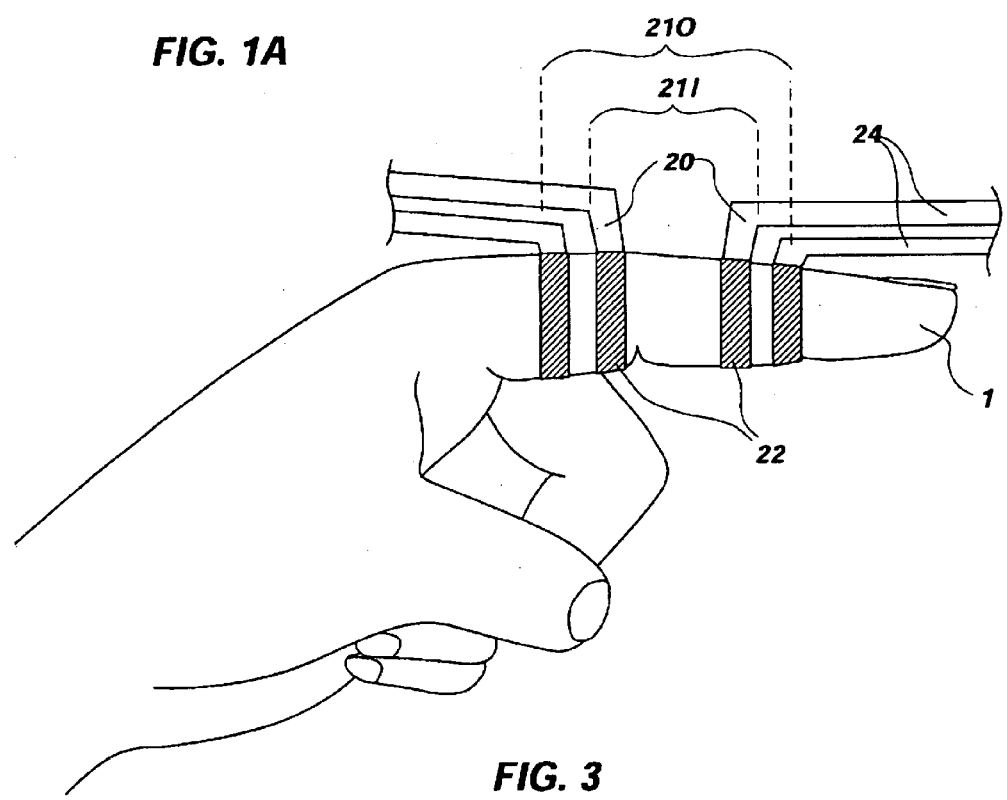
FIG. 3 is a perspective view depicting four of the electrodes shown in FIG. 2 partially wrapped around a finger of a patient.

An example of the use of electrodes 20 is illustrated in FIG. 3, which shows first members 22 of four electrodes 20 in contact with and being wrapped around a body part, in this case a finger 1, at which hematocrit is to be measured in accordance with teachings of the present invention. As depicted, electrodes 20 are arranged in outer and inner sets 21O and 21I, respectively, with electrodes 20 of inner set 21I spaced apart from one another and electrodes 20 of outer set 21O positioned adjacent and outside of electrodes 20 of inner set 21I. The adjacent electrodes 20 of inner set 21I and outer set 21O are spaced more closely to one another than electrodes 20 of inner set 21I.

Figure 4:
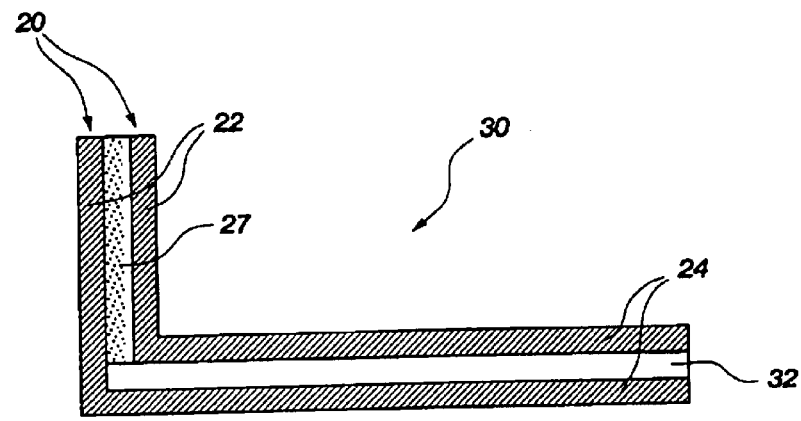
FIG. 4 is a top view of an embodiment of an element of an apparatus incorporating teachings of the present invention that includes two of the electrodes shown in FIG. 2 being carried by a substantially planar substrate.

FIG. 4 depicts an assembly 30 including two electrodes 20 that are partially carried upon a pliable substrate 32. As illustrated, pliable substrate 32 supports first members 22 of electrodes 20. Exemplary materials from which pliable substrate 32 may be fabricated include, without limitation, fabrics, polymers, and other flexible materials. As shown in FIG. 4, pliable substrate 32 also includes a retention component 27, in this case a quantity of adhesive material, between first members 22. Adhesive material 27 is preferably a pressure sensitive adhesive that will maintain contact between first members 22 and the body part at which hematocrit is to be measured, as well as to maintain the positions of first members 22 relative to the body part.

Figure 5:
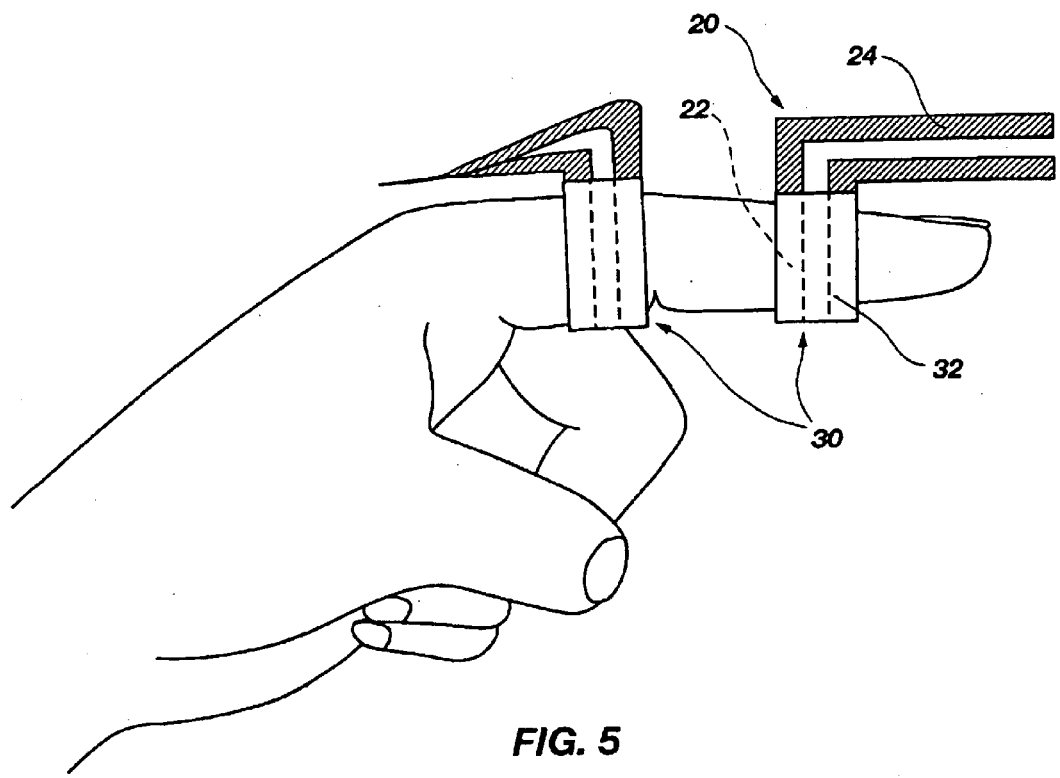
FIG. 5 is a perspective view depicting two of the elements depicted in FIG. 4 secured to a finger of a patient.

An example of the use of assembly 30 for effecting the method of the present invention is illustrated in FIG. 5. As shown, two assemblies 30 are positioned upon a body part, in this case a finger 1, with first members 22 of electrodes 20 contacting the body part. As depicted, assemblies 30 are spaced a greater distance apart from one another than are electrodes 20 of each assembly 30.

Figure 6:
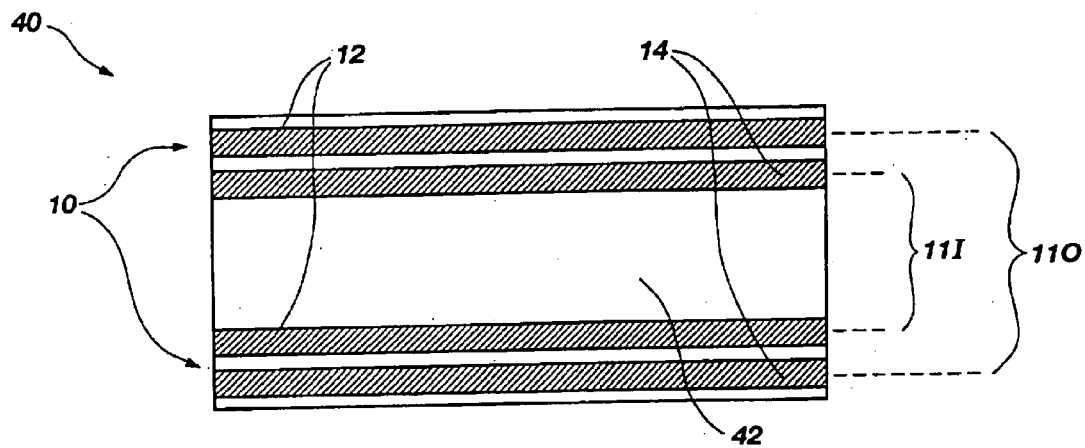
FIG. 6 is a top view of another embodiment of apparatus according to the invention, including four of the electrodes shown in FIG. 1 secured to a substantially planar, pliable substrate.

Another embodiment of an electrode assembly 40 that is useful in carrying out the method of the present invention is shown in FIG. 6. Assembly 40 includes a pliable substrate 42, similar to that depicted in FIG. 4 and described with reference thereto, and four electrodes 10 carried thereby. As illustrated, electrodes 10 are oriented upon pliable substrate 42 in substantially mutually parallel relation. Assemblies with electrodes 10 that are not oriented parallel to one another are, however, also within the scope of the present invention. Electrodes 10 are arranged in an inner set 11I and an outer set 11O. Electrodes 10 of inner set 11I are positioned adjacent one another and electrodes 10 of outer set 11O are positioned outside of electrodes 10 of inner set 11I, with electrodes 10 of inner set 11I being spaced apart a greater distance than each electrode 10 of inner set 11I and the adjacent electrode 10 of outer set 11O. Second ends 14 of electrodes 10 are preferably configured to couple with an electrical connector of a known type, such as connector 44 depicted in FIG. 7.

Figure 7:
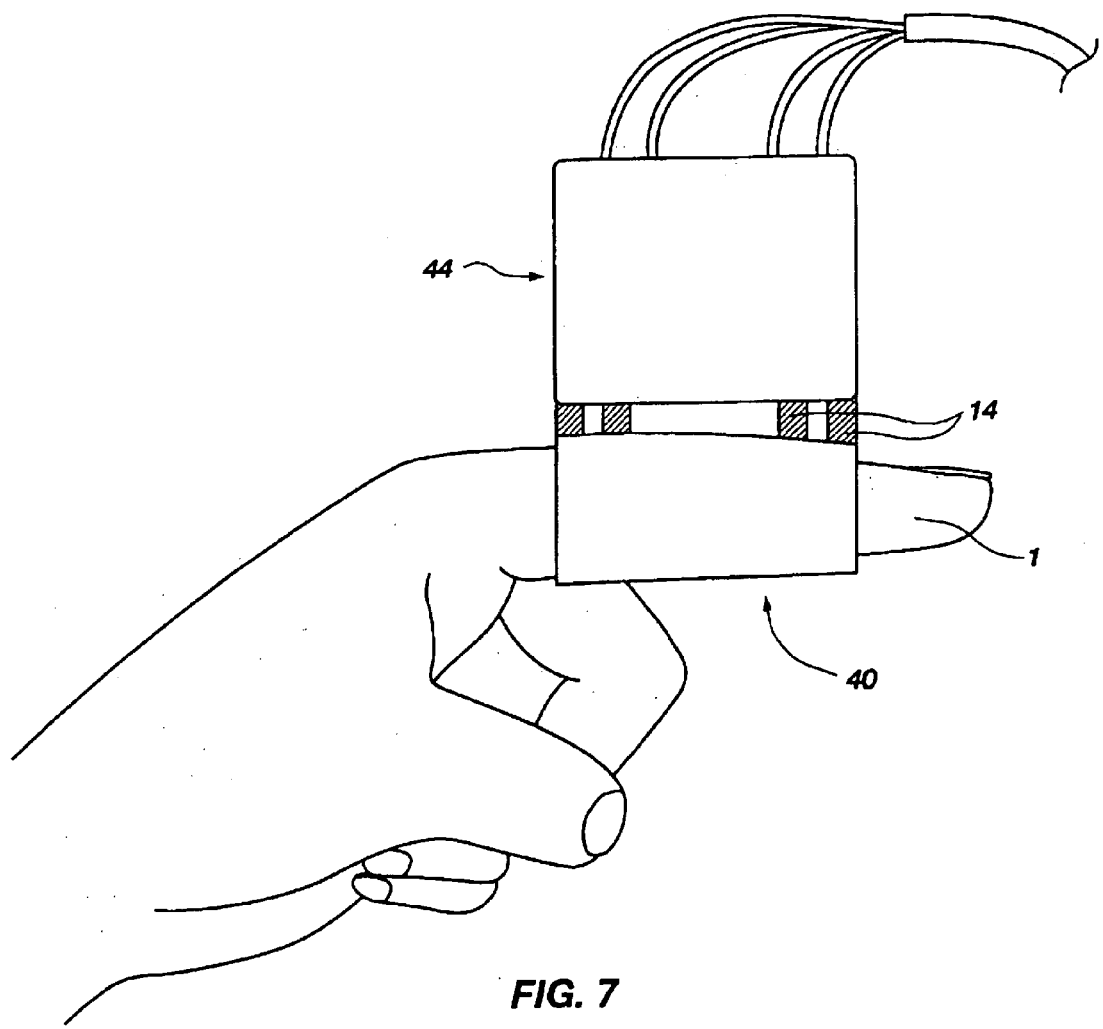
FIG. 7 is a perspective view illustrating the apparatus of FIG. 6 secured to a finger of a patient and electrically connected to external electronic componentry by way of an exemplary connector.

FIG. 7 illustrates the manner in which assembly 40 is used in determining the hematocrit of a patient. Assembly 40 is positioned relative to a body part of a patient, such as finger 1, with first ends 12 of electrodes 10 (see FIG. 6) in contact with the body part. As shown, first ends 12 of electrodes 10 are at least partially wrapped around finger 1. Second ends 14 of electrodes 10 extend beyond an outer periphery of pliable substrate 42 and are coupled with corresponding terminals of an electrical connector 44, which communicates with external electronic components (not shown) that are used to effect the method of the present invention.

Figure 8:
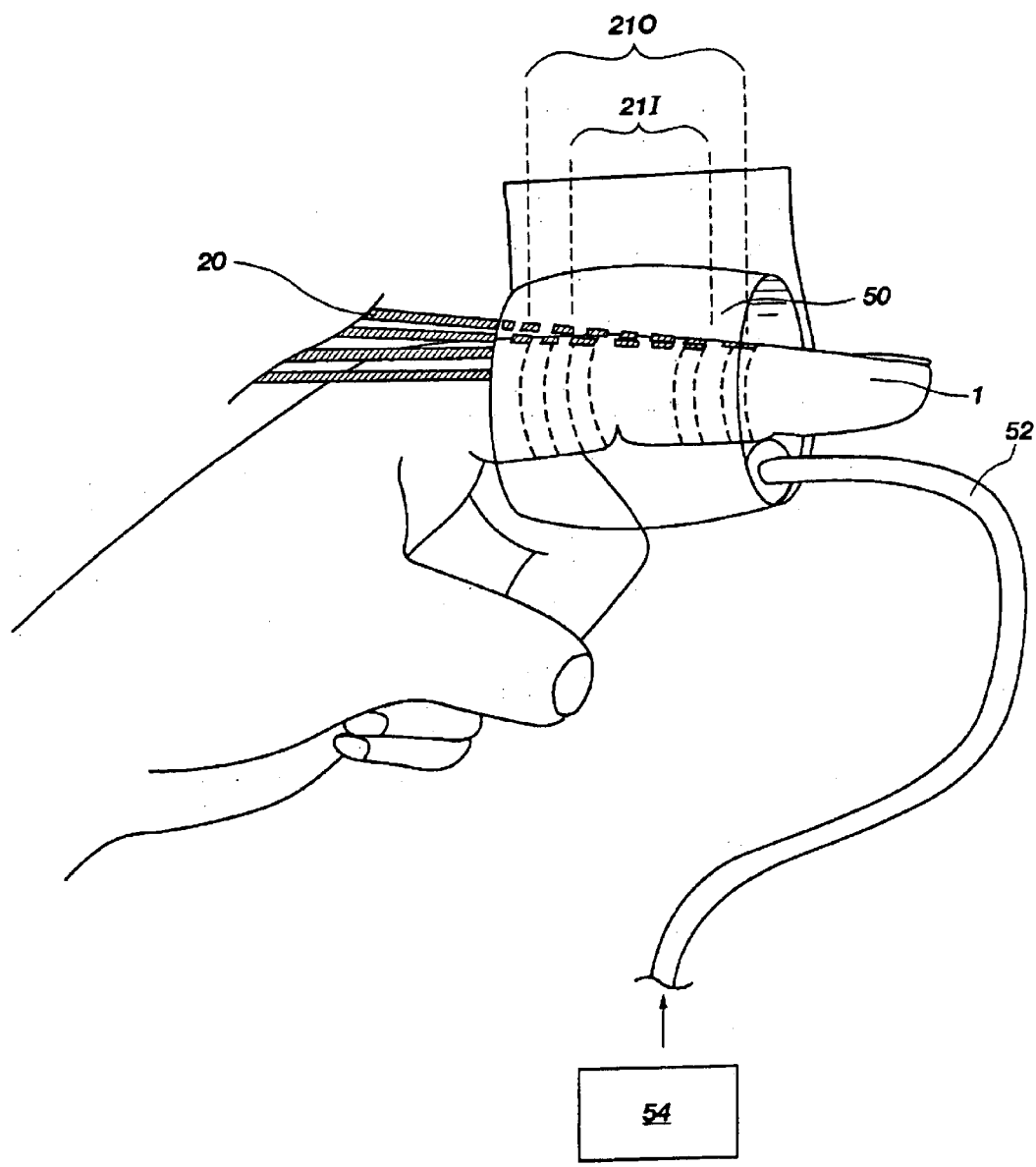
FIG. 8 is a perspective view illustrating four of the electrodes shown in FIG. 2 secured to a finger of a patient with a bladder embodiment of a separate pressurization component secured around the electrodes to the finger.

An apparatus according to the present invention may also include a pressurization device, such as an inflatable bladder 50 illustrated in FIG. 8. Inflatable bladder 50 may be of any type known in the art, such as an infant blood pressure cuff, which may be secured around a body part, such as a finger, at which hematocrit is to be measured by known means, such as complementary hook and loop type fasteners. As depicted, bladder 50 is separate from electrodes 20, which are wrapped around a finger 1 in substantially the same manner as that depicted in and described with reference to FIG. 3. Bladder 50 is at least partially wrapped around a body part at which hematocrit is to be measured, such as finger 1, so as to apply pressure thereto in order to facilitate the hematocrit measurement. Bladder 50, as well as any other embodiment of pressurization component used in the present invention, may be positioned relative to the body part so as to apply pressure between the innermost pair 21I of electrodes 20. Preferably, bladder 50 or another pressurization component abuts or at least partially overlaps each electrode of innermost pair 21I so as to apply pressure to an entire portion of the body part located between innermost pair 21I.

Bladder 50 communicates with an external pressure source 54 as known in the art, such as by use of a conduit 52, such as a tube. As an example of the manner in which the internal pressure of bladder 50 may be increased, air or another fluid may be supplied to bladder 50 from external pressure source 54 by way of conduit 52. As the internal pressure of bladder 50 increases, pressure is applied to the body part at which hematocrit is to be measured. Although FIG. 8 depicts bladder 50 as being wrapped around finger 1 and all four electrodes 20 thereon, bladder 50 may be positioned elsewhere on finger 1 or another body part, such as between electrodes 20 of inner set 21I or over two adjacent electrodes 20.

Figure 9:
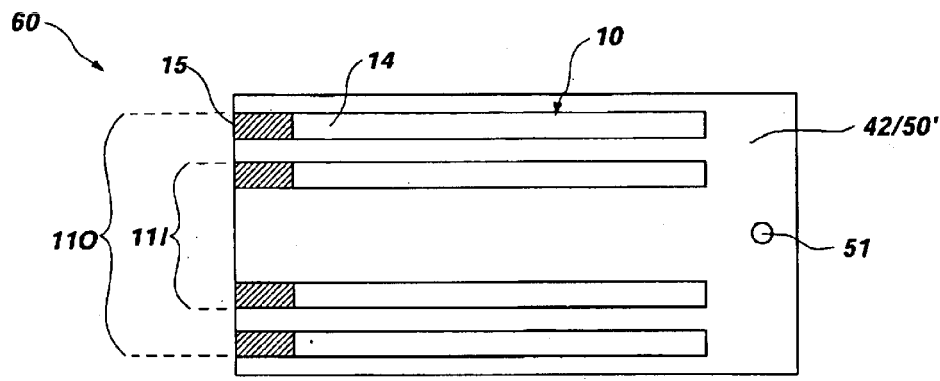
FIG. 9 is a top view of an embodiment of an apparatus of the present invention that includes four of the electrodes shown in FIG. 1 carried on a surface of a substantially planar pliable bladder.

FIG. 9 illustrates another embodiment of an assembly 60 that may be used to measure hematocrit in accordance with teachings of the present invention. Apparatus 60 includes a pliable substrate 42, which comprises a bladder 50' that may be pressurized. Bladder 50' includes a port 51 to facilitate connection to an external pressure source, such as external pressure source 54 depicted in FIG. 8. For example, an end of a conduit, or tube, may be inserted into port 51 and retained therein by way of an externally protruding, circumferentially extending rib formed around the end of the conduit. Apparatus 60 also includes four electrodes 10 carried upon a surface of bladder 50'. As depicted, apparatus 60 includes four electrodes 10 that are arranged in mutually parallel relation to one another. Electrodes 10 are arranged in two sets, including an inner set 11I and an outer set 11O. Electrodes 10 of inner set 11I are spaced apart from one another, while electrodes 10 of outer set 11O are positioned outside of electrodes 10 of inner set 11I, adjacent thereto, and spaced apart therefrom a lesser distance than electrodes 10 of inner set 11I are spaced apart from one another. Preferably, second end 14 of each electrode 10 includes a terminal end 15 that extends beyond an outer periphery of bladder 50' so as to facilitate electrical connection of electrodes 10 and assembly 60 to external electronic componentry (not shown) that effects the method of the present invention. For example, terminal ends 15 may at least partially wrap around a peripheral edge of bladder 50'.

Figure 10:
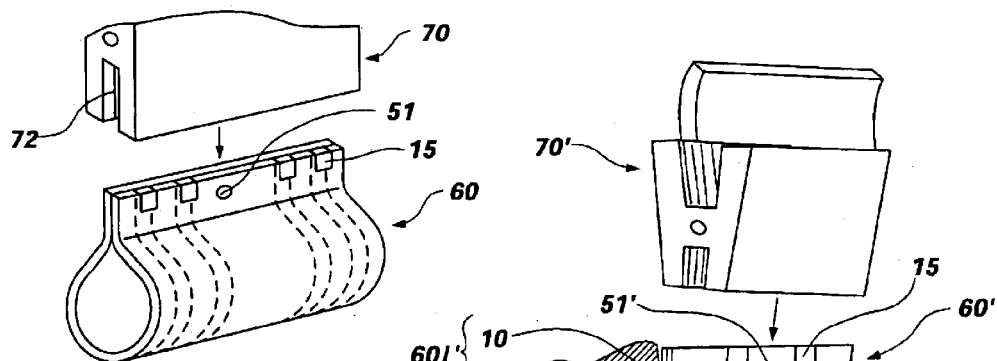
FIG. 10 is a perspective view of the assembly of the apparatus shown in FIG. 9 and an electrical connector therefor.

FIG. 10 illustrates connection of assembly 60 to an electrical connector 70 of a type known in the art. Electrical connector 70 includes terminals 72 that correspond to terminal ends 15 of electrodes 10 to connect electrodes 10 with the appropriate external electronic componentry (not shown).

Figure 11:
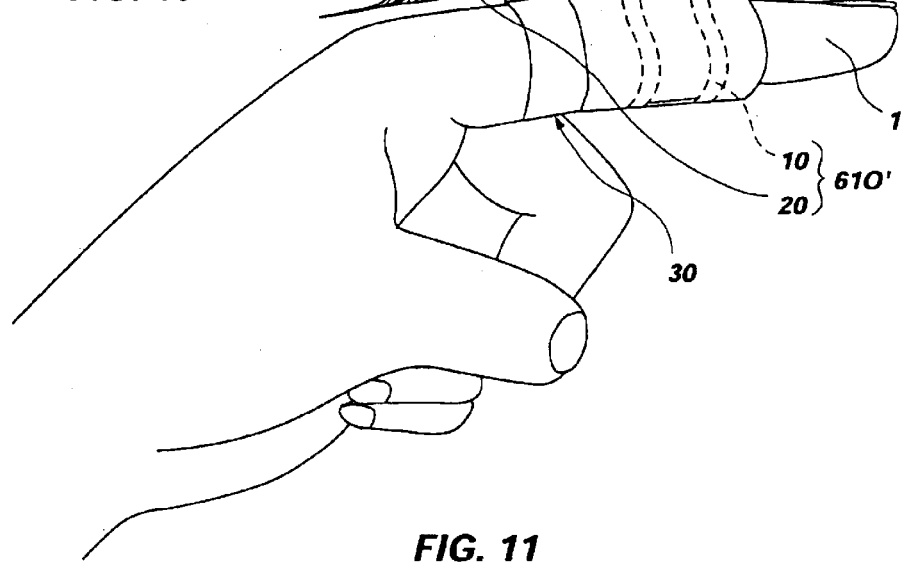
FIG. 11 is a perspective view illustrating, wrapped around a finger of a patient, an element of yet another embodiment of an apparatus that includes a substantially planar bladder member with two of the electrodes shown in FIG. 1 secured to the surface thereof, as well as the element of FIG. 4 wrapped around an adjacent portion of the finger.

FIG. 11 illustrates an assembly 60', which is a variation of assembly 60, that includes two electrodes 10, as well as an electrical connector 70' configured to connect assembly 60' to external electronic componentry (not shown) that facilitates the determination of a patient's hematocrit in accordance with teachings of the present invention. When assembly 60' is employed, two additional electrodes, such as electrodes 20 of assembly 30 must also be brought into contact with a body part, such as finger 1, at which hematocrit is to be measured. The outermost electrode 20 of assembly 30 and the outermost electrode 10 of assembly 60' comprise an outer set 61O', while the innermost electrode 20 of assembly 30 and the adjacent electrode 10 of assembly 60' comprise an inner electrode set 61I' to facilitate the measurement of hematocrit in accordance with teachings of the present invention. The pliable substrate of assembly 60' is an inflatable bladder 50' that includes a port 51' through which bladder 50' may be pressurized and depressurized.

Figure 12:
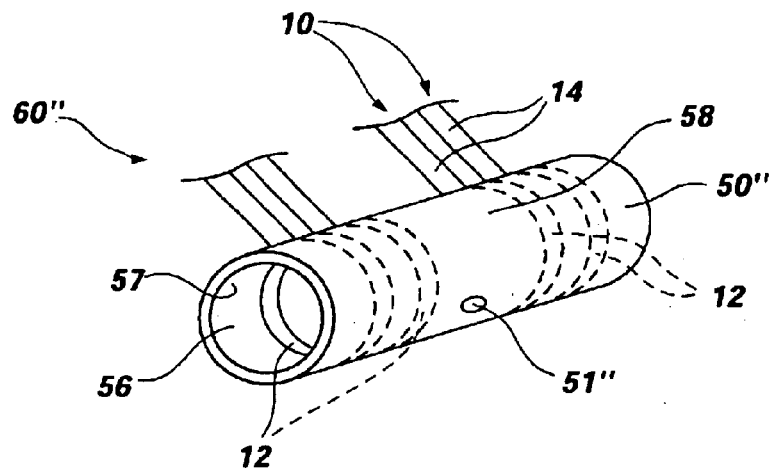
FIG. 12 is a perspective view of yet another embodiment of apparatus including electrodes shown in FIG. 1 carried on an inner surface of a tubular bladder configured to at least partially receive a finger.

FIG. 12 illustrates yet another embodiment of an assembly 60" for measuring hematocrit in accordance with the method of the present invention. Assembly 60" includes an inflatable bladder 50" having a tubular shape. Bladder 50" includes a receptacle 56 configured to at least partially receive a body part, such as a finger, at which hematocrit is to be measured. First ends 12 of electrodes 10 are at least partially carried upon an inner surface 57 of bladder 50" and exposed to receptacle 56. Thus, upon at least partial insertion of a body part into receptacle 56, first ends 12 of electrodes 10 contact the body part. Second ends 14 of electrodes 10 are exposed at and may extend beyond an outer surface 58 of bladder 50" so as to facilitate connection of assembly 60" to external electronic componentry that effects the method of the present invention. Bladder 50" also includes a port 51" that facilitates pressurization and depressurization of bladder 50".

Figure 13:
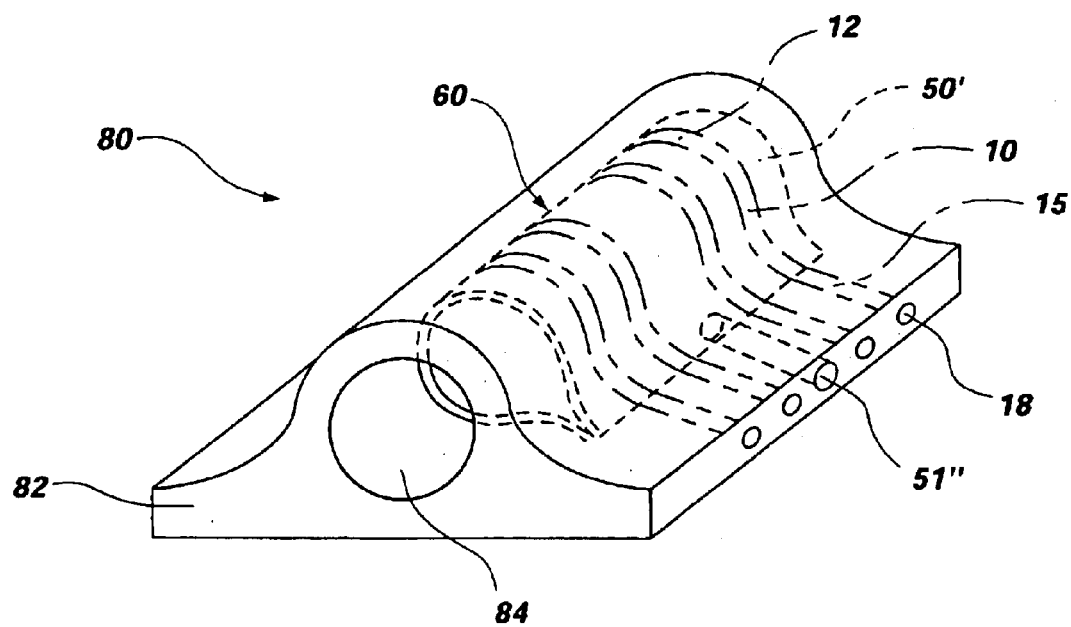
FIG. 13 is a perspective view of a rigid member including a receptacle at least partially lined by the apparatus shown in FIG. 9.

Yet another apparatus 80 configured to position electrodes 10 in contact with a body part at which hematocrit is to be measured and to apply pressure to the body part in accordance with teachings of the present invention is illustrated in FIG. 13. Apparatus 80 includes a rigid member 82, which may be formed from, for example, a polymer, that includes a receptacle 84 configured to at least partially receive a body part at which hematocrit is to be measured. Disposed within receptacle 84 is an assembly 60, such as that illustrated in and described with reference to FIG. 9. Assembly 60 is disposed within receptacle 84 such that upon at least partial insertion of a body part, such as a finger, within receptacle 84, first ends 12 of all four electrodes 10 of assembly 60 contact the body part. Preferably, bladder 50' of assembly 60 also contacts the body pressure in a manner that will allow for the application of pressure of the body part upon pressurization of bladder 50' through port 51". Terminal ends 15 of electrodes 10 communicate with electrical connectors 18 of a known type that are held within rigid member 82 and that facilitate connection of electrodes 10 to external electronic componentry (not shown) to effect a determination of hematocrit in accordance with the present invention.

Figure 14:
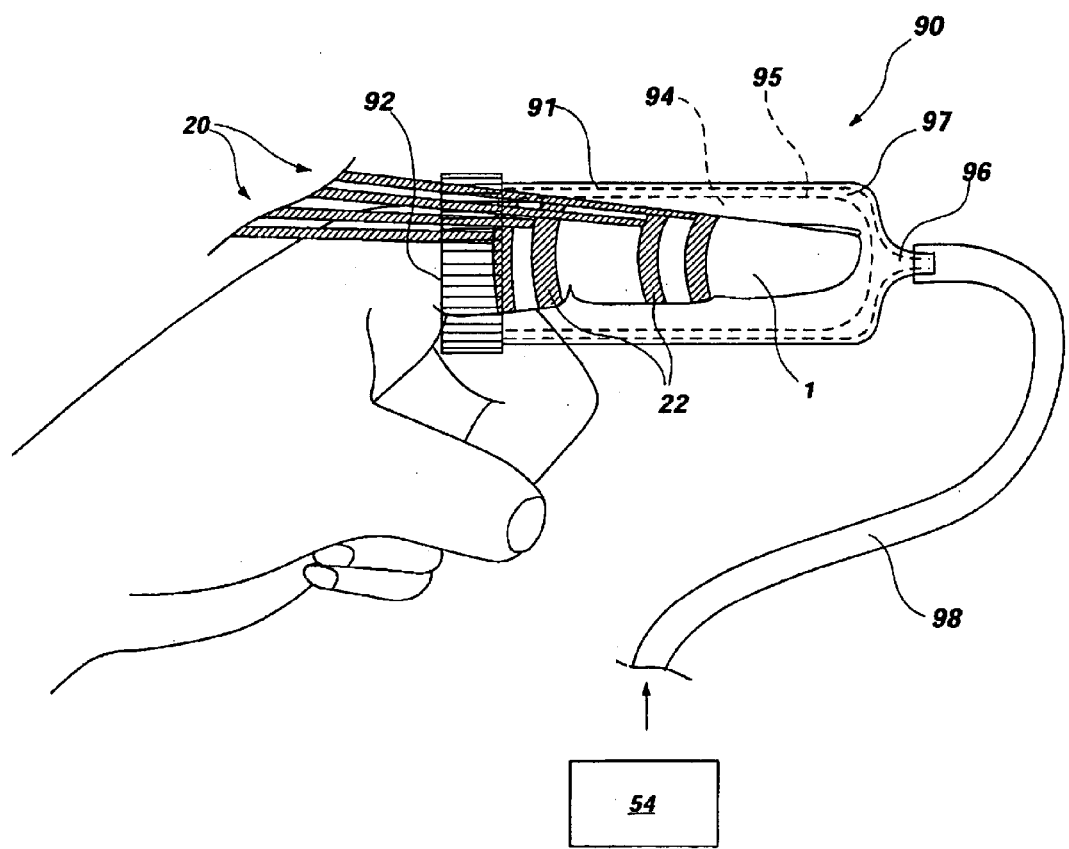
FIG. 14 is a perspective view of another embodiment of a pressurization component of the present invention, including a close-ended pressure chamber configured to receive a finger of a patient.

FIG. 14 illustrates a pressurization chamber 90 that may be used to effect a hematocrit determination in accordance with the present invention. As illustrated, pressurization chamber 90 includes a generally cylindrical, hollow, rigid member 91, a flexible, pliable member 95 therein, and a receptacle 94 within pliable member 95. Receptacle 94 is configured to at least partially receive a body part, such as finger I, at which hematocrit is to be determined. The body part may be inserted into receptacle 94 through a first end 92 of pressurization chamber 90. Pressurization chamber 90 also includes pressurization port 96 through which a pressurization bladder 97, formed by pliable member 95 and rigid member 91, may be either positively or negatively pressurized. As air or gas is introduced into pressurization bladder 97, pliable member 95 expands into receptacle 94, decreasing the volume thereof. Thus, as air or gas is introduced into pressurization bladder 97, pliable member 95 is forced against a finger 1 or other body part disposed within receptacle 94, applying pressure thereto. As shown in FIG. 14, pressurization port 96 is configured to be coupled with a pressurization conduit 98, such as a tube, that communicates with an external pressure source 54. While FIG. 14 illustrates a finger 1 with first ends 22 of each of four electrodes 20 wrapped at least partially therearound disposed within receptacle 94, a portion of finger 1 or another body part with fewer than four electrodes 20 contacting same may be disposed within receptacle 94.

Figure 15:
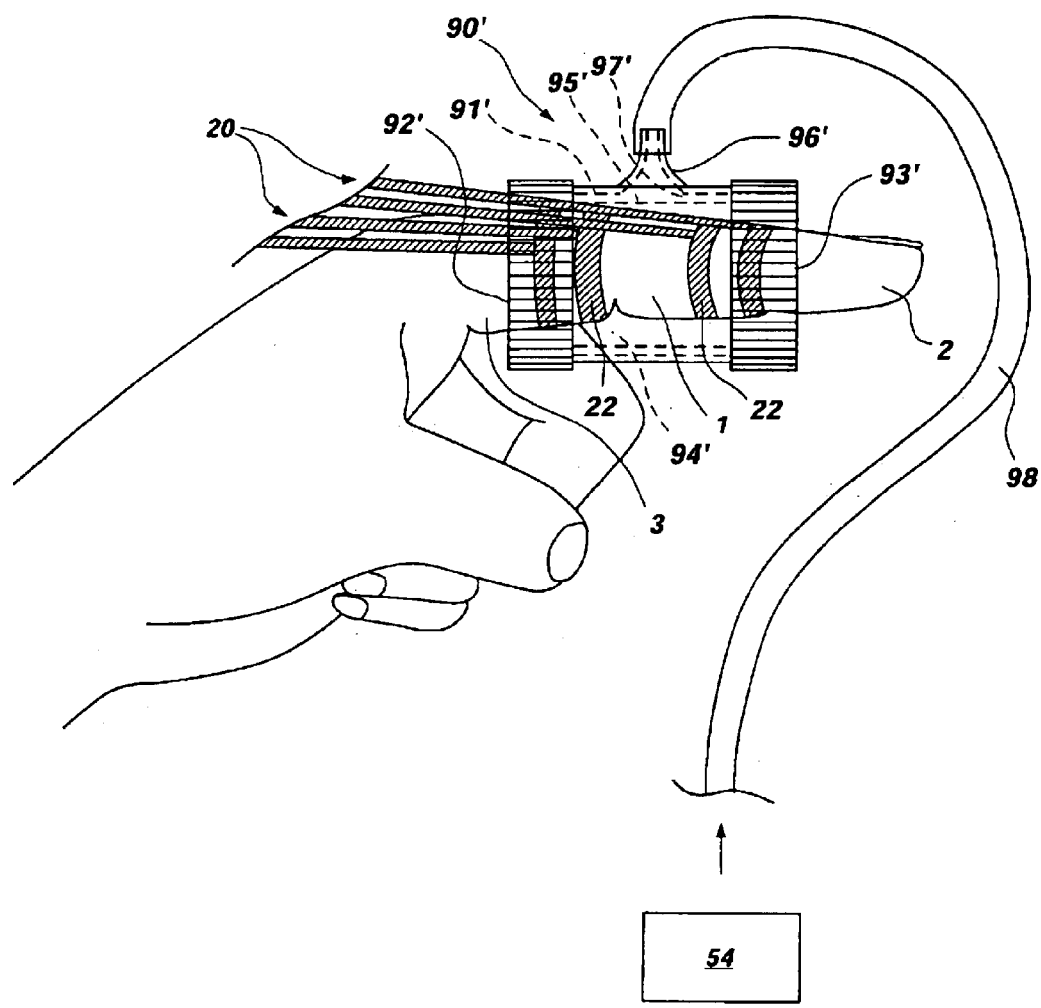
FIG. 15 is a perspective view of still another embodiment of a pressurization component incorporating teachings of the present invention, including a pressure chamber with two open ends, through which a portion of a finger of a patient extends, and depicting a finger and the portions of four of the electrodes shown in FIG. 2 in contact therewith inside the pressure chamber.

Another pressurization chamber 90' that may be used in the method of the present invention is illustrated in FIG. 15. Pressurization chamber 90' includes a generally cylindrical, hollow, rigid member 91', and a flexible, pliable member 95' within rigid member 91'. Pliable member 95' forms a receptacle 94' within pressurization chamber 90'. A pressurization bladder 97' is formed between rigid member 91' and 95'. Pressurization chamber 90' also includes two opposed, open ends 92' and 93'. Ends 92' and 93' are both continuous with a receptacle 94' of pressurization chamber 90'. Pressurization chamber 90' communicates with an external pressure source 54 by way of a conduit 98 connected to a pressurization port 96' of pressurization chamber 90'. Pressurization bladder 97' may be pressurized by introducing air, gas, or another pressurization medium therein through pressurization port 96'. As a positive pressure forms within pressurization bladder 97', pliable member 95' is forced toward receptacle 94', decreasing the volume of receptacle 94'. Thus, as positive pressure is introduced into pressurization bladder 97', pliable member 95' is forced onto a finger 1 or other body part disposed within receptacle 94' and applies pressure thereto.

Figure 16:
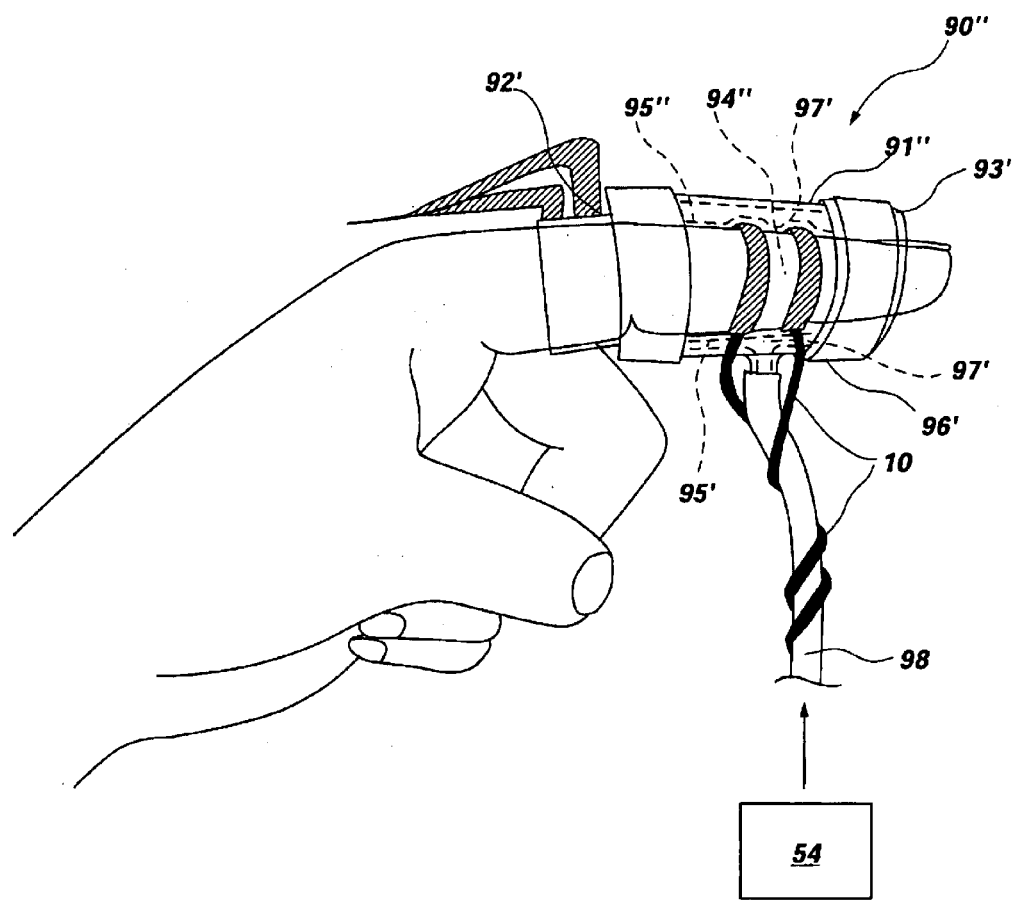
FIG. 16 is a perspective view illustrating the pressure chamber of FIG. 15 being disposed around a finger of a patient and around portions of two electrodes of the type shown in FIG. 1 that contact the finger, as well as the element of FIG. 4 being wrapped around an adjacent portion of the finger.

As illustrated in FIG. 15, pressurization chamber 90' is configured to partially receive finger 1, with a base 3 of finger 1 extending through end 92' and a tip 2 of finger 1 extending through end 93'. FIG. 15 also shows that first ends 22 of all of four electrodes 20 that are wrapped around finger 1 are located within chamber 94'. Although FIG. 15 depicts all four electrodes 20 contacting finger 1 as being disposed at least partially within chamber 94', as shown in FIG. 16, finger 1 or another body part at which hematocrit is to be measured may be positioned within a receptacle 94" of a pressurization chamber 90" such that fewer than four electrodes 10 are located within chamber 94". As illustrated, electrodes 10 extend through rigid member 91" and pliable member 95" of pressurization chamber 90".

System and Methods for Noninvasively Measuring Hematocrit

Overview

An overview of one exemplary structure of a system incorporating teachings of the present invention will be followed by a discussion of its methods for hematocrit measurement.

Figure 17:
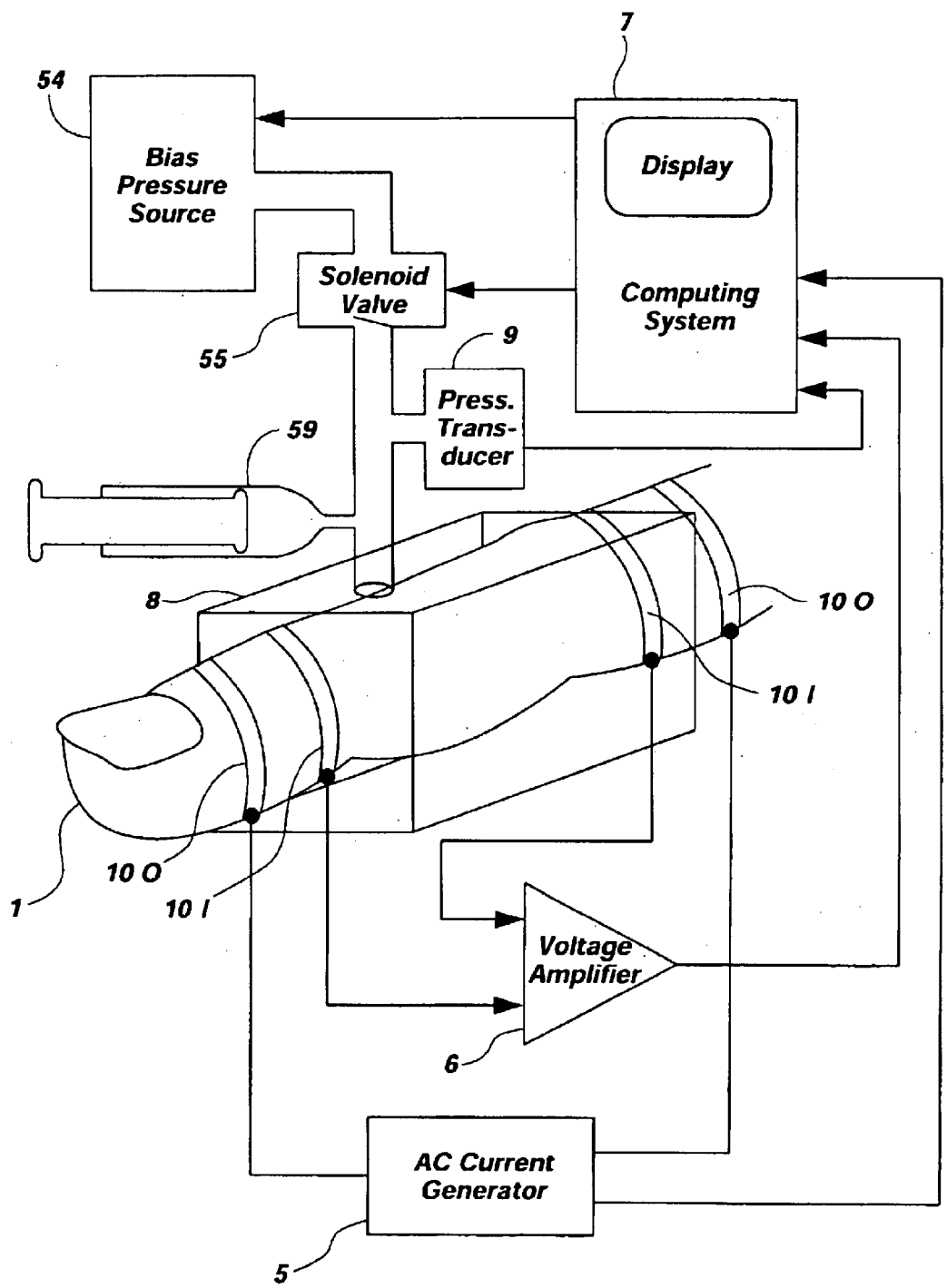
FIG. 17 is a block diagram of a hematocrit measurement system in accordance with this invention.

An embodiment of the present invention is shown in FIG. 17. In this embodiment, the pulsatile impedance and pulsatile pressure are measured in a chamber surrounding a patient's finger. Although a finger has been chosen as an exemplary body part to illustrate this embodiment, it is important to note that other body parts may be used. In addition, although FIG. 17 illustrates some specific components, any assemblage of electrodes, pressurization apparatus, and other devices that incorporate teachings of the present invention may be used in the system to effect the hematocrit determination method of the invention.

An array of electrodes 10 is placed on a finger 1 with the outer electrodes 10O separated as widely as possible and the inner electrodes 10I each separated by approximately 5.0 mm from the closest of outer electrodes 10O and separated from each other by a distance as far as possible but necessarily limited by the length of finger 1.

The outer electrodes 10O are driven by an alternating current generator 5 which may be set to deliver a constant current at a frequency in the approximate range of 10 kHz to 200 kHz.

The optimum frequency for this system likely lies in the previously-mentioned range to achieve the goals of maximum current with no discernible neuromuscular stimulation and low phase difference between the current and voltage applied to the electrodes. While test results on an early prototype of this invention indicate that 100 kHz is appropriate for achieving satisfactory results, it is possible that another frequency may result in a more practical implementation.

The inner electrodes 10I are connected to the input of a high impedance voltage amplifier 6 which senses the voltage between these electrodes. Both the current generator 5 and the amplifier 6 are connected to a computing system 7, which combines these electrical signals with other signals from the pressure sensing apparatus (described below) to compute and display hematocrit. The computing system 7 also has the purpose of controlling the automated operation of the measurement apparatus. The details of the computing system 7 are not depicted in FIG. 17 or in the description of this invention because any of a number of configurations, including, but not limited to, an appropriately programmed PC-type computer with an analog-to-digital converter and an output port control interface, or a dedicated monitor, will suffice for performance of this function.

A sealed pressure chamber 8 surrounds the finger with air tight, pressure-withstanding seals at its distal and proximal. These seals are located over, or in very close proximity to, the inner electrodes 10I. The first purpose of this chamber 8 is to contain the air in the closed volume of the chamber around the finger so that small pulse pressure rises occur in the chamber 8 when blood from the arterial system of the patient's circulation is pulsed into the finger. The second purpose of this chamber 8 is to contain an externally applied bias pressure which causes blood vessels in the part of the finger that is enclosed by the chamber 8 to partially collapse. This partial collapse of the vessels results in greater blood flow into the finger on each cardiac pulse. In turn, the larger blood flow pulses, created as a result of the bias pressure, cause greater pressure pulses to occur within the chamber and greater voltage pulses to occur between the inner impedance sensing electrodes 10I. It should be understood that the electrodes 10 may be integral with the chamber 8, or may be separate from the chamber 8 and applied to the finger independently of its insertion into the chamber.

A pressure transducer 9 is pneumatically connected to the pressure chamber 8 and electrically connected to the computing system 7 for sensing the bias pressure and the pulse pressure from which blood volume on each pulse is computed, and for transmitting signals representative of pressure to the computing system 7. Also connected pneumatically to the pressure chamber 8 is a bias pressure source 54 with a solenoid valve 55 controlled by the computing system 7. This valve 55 allows enough flow from the bias pressure source 54 to achieve the desired bias pressure, then shuts off to lock the bias pressure in. The pressure source 54 may be of any configuration having the ability to supply air at a pressure as high as approximately 200 mmHg above the ambient atmospheric pressure. The level of pressure supplied may optionally be controlled by the computing system 7.

Also connected to the pressure chamber 8 is a calibration device 59 which can inject a precisely known volume of air into the chamber 8 to calibrate the pressure change that represents a given volume. This calibration device 59 may be as simple as a small calibrated medical syringe, as shown in FIG. 17, which can be manually operated, or it can be a more complex device, controlled by the computing system 7, capable of producing precise volume pulses of close to the same magnitude as the cardiac pulses for dynamic calibration.

A Method of Measurement

It is known by those skilled in the art of physiological impedance measurements that the blood pulsed into a tissue space between a pair of sensing electrodes upon each heartbeat causes a pulsatile decrease in impedance. The change in impedance over time due to the heartbeat can be observed on an oscilloscope to obtain a picture called the impedance waveform. This waveform, when inverted and appropriately scaled, has approximately the same shape as does the change in blood volume over time due to the heartbeat. This similarity of waveforms suggests that the change of impedance is due to the change in volume and could be used to measure the volume change.

An equation relating the volume change, $\Delta V$, to the impedance change, $\Delta Z$, has been developed and has been reported by Geddes and Baker in "Principles of Applied Biomedical Instrumentation," second edition, John Wiley and Sons, New York (1975). This equation is:

$$\Delta V = \rho L^2 \Delta Z / Z_0^2 \quad (1)$$

where $\Delta V$ is the change in blood volume at any point in time, $\Delta Z$ is the change of impedance at the same point in time, $\rho$ is the resistivity of the blood, L is the distance between the impedance sensing inner electrodes 10I, and $Z_0$ is the baseline impedance at the beginning of each pulse.

The previously described equation (1) can be rearranged to solve for $\rho$, the resistivity, which we know to be dependent upon hematocrit:

$$\rho = \Delta V Z_0^2 / L^2 \Delta Z \quad (2)$$

We now observe that all of the values needed for the computation of $\rho$ (i.e., $\Delta V$, $Z_0$, L, and $\Delta Z$) are measurable in the system previously described. Specifically, $\Delta V$ is measured by the pressure transducer 9 as the change of volume in the pressure chamber 8, $Z_0$ and $\Delta Z$ are measured by the voltage amplifier 6, and L is the measured distance between the inner sensing electrodes 10I.

Having $\rho$, it is now straightforward to compute hematocrit. In their paper "The Specific Resistance of Blood at Body Temperature," Medical and Biological Engineering, 11:336-339 (1973), Geddes and Sadler have experimentally derived and reported mathematical relationships between blood resistivity $\rho$ and hematocrit H in both simple algebraic and exponential forms. The algebraic form is:

$$\rho = (58 + 0.435H)/(1 - 0.01H) \quad (3)$$

where H is percent hematocrit. This can be solved for H in terms of $\rho$ as:

$$H = (\rho - 58)/(0.01\,\rho + 0.435) \quad (4)$$

Having applied this last equation (4), using the value of ρ determined form the impedance and volume measurements, we now have hematocrit H, which was our original objective.

To obtain maximum accuracy in application of the equations shown above, a very accurate measurement of blood volume change (ΔV) should be made. This is accomplished by comparing, in the computing system 7, the pressure change within the chamber 8 on the finger against the pressure change that results from a known change in volume imposed by the calibration device 59. A calibration device 59 controlled by the computing system 7 can be adjusted to produce precisely controlled volume changes of approximately the same magnitude as those produced by the blood pulses. This method of calibration should produce the greatest accuracy of hematocrit measurement.

Optionally, the accuracy of both the impedance and direct volume measurements can be improved by producing larger arterial pulses in the finger. The imposition of a bias pressure in the chamber 8, having a magnitude above a substantial fraction of the systolic blood pressure at the finger, and preferably having a magnitude equal to the mean arterial blood pressure in the finger, has been shown experimentally to increase the pulse volume by as much as a factor of ten. The increase in pulse volume achieved by this means increases the accuracy of the hematocrit measurement by improving the signal-to-noise ratios on both the impedance and pressure channels going to the computing system 7. More importantly, the arterial component of the pulse volume becomes greater with respect to pulsatile volume changes in other vessels in the finger (such as the capillaries), which makes the derived hematocrit more nearly a true value.

Pattern Recognition Algorithms

Experiments have determined that the impedance pulse in the finger is often very weak compared to the pressure pulse, both of which are simultaneously measured in application of this invention. In detecting the impedance pulse by measuring the voltage on the inside electrode pair 10I, it has been found that there is often a large noise voltage that obscures the signal and diminishes the accuracy of the measurement. In such situations, it is our practice to filter the noisy signal using an analog filter circuit or, alternatively, using a digital filtering algorithm, implemented in the computing system 7. One type of digital filter that may be used employs the assumption that the general shape of both the impedance pulse waveform and the pressure pulse waveform are the same. When this assumption is made, it follows that both signals must have the same frequency components. These facts, i.e., that both signals are of the same shape and frequency content, allow the use of adaptive filtering algorithms implemented either as matching filters in the time domain or frequency window filters in the frequency domain wherein the optimum filter parameters are derived from the characteristics of the relatively clean pressure signal waveform. In other words, the filtering algorithms use the relatively clean pressure signal waveform as a template for the relatively noisy impedance signal waveform to filter out noise.

Another Embodiment of the Method of Measurement

The original method of hematocrit determination, described by Kaminsky in the '808 Patent referenced above, was subject to limitations resulting from the very small blood volume pulses occurring in the finger and the noisy impedance signals. Application of the bias pressure method for enhancing the pulses, as taught by the present invention, as well as application of the filtering method described in the preceding paragraph, improves the accuracy of this two-frequency method, as well as any other multi-frequency method which depends upon the blood pulse for discrimination of the arterial blood impedance component. Any such implementation which uses a pressure chamber (or cuff) in conjunction with an electrode array to measure the pulse volume, to obtain a pressure pulse signal for deriving adaptive filter parameters, or to impose a bias pressure for enhancing the arterial pulse, is considered to be within the scope of this invention.

Application of equation (2) described above to two separate frequencies allows us to obtain the following ratio:

$$(\rho_L/\rho_H)=(Z_L^2/Z_H^2)\cdot(\Delta Z_H/\Delta Z_L) \tag{5}$$

where $\rho_L$ is the resistivity of blood at the lower of the two frequencies, $\rho_H$ is the resistivity of the blood at the higher of the two frequencies, $Z_L$ is the baseline impedance for the low frequency, $Z_H$ is the baseline impedance for the high frequency, $\Delta Z_H$ is the change in impedance at a point in time for the high frequency, and $\Delta Z_L$ is the change in impedance at a corresponding point in time for the low frequency.

Notice that equation (5) offers the distinct advantage of canceling the geometric factors ΔV and L. By choosing a high frequency between 1 MHz and 10 MHz, the hematocrit H can be adequately represented as a function of $(\rho_L/\rho_H)$. The measurement of $(\rho_L/\rho_H)$ from equation (5) can be represented in terms of measurable voltages and currents by:

$$(\rho_L/\rho_H)=(\Delta\text{Volt}_H/\Delta\text{Volt}_L)\cdot(\text{Volt}_L^2/\text{Volt}_H^2)\cdot(I_H/I_L) \tag{6}$$

where ΔVolt, Volt, and I represent measurable pulse voltages, baseline voltages, and currents, respectively.

Since $I_H$ and $I_L$ are constant current sources which can be placed under instrument control, equation (6) can be simplified to:

$$(\rho_L/\rho_H)=C\cdot(\Delta\text{Volt}_H/V_H^2)/(\Delta\text{Volt}_L/\text{Volt}_L^2) \tag{7}$$

where $C=I_H/I_L$ is a known constant.

An In-Vivo Model for Relating $(\rho_L/\rho_H)$ to Hematocrit

A representation of $(\rho_L/\rho_P)$, as published by Geddes and Sadler ("The Specific Resistance of Blood at Body Temperature," Med. and Biol. Eng., 336–339, May, 1973), is given by:

$$(\rho_L/\rho_P)=[1+(f-1)\cdot H]/(1-H) \tag{8}$$

where $\rho_P$ is the resistivity of plasma, and f is a form factor (determined by Geddes and Sadler to be 1.75 for human red blood cells when their orientation is random). The effect of frequency on blood resistivity is explained by noting that the red blood cell membrane behaves as an insulator at low frequencies, causing $\rho_L$ to be predictably higher with increasing hematocrit H. However, at frequencies of about 10 MHz and higher, the red blood cell membrane reactance is virtually eliminated, which causes the intracellular fluid to participate fully in the blood impedance measurement. This reduces the $\rho_H$ sensitivity to hematocrit H. The sensitivity of $\rho_H$ to hematocrit H would be virtually eliminated at frequencies of 10 MHz and higher if it were not for the fact that the resistivity of the intracellular fluid $(\rho_{RBS})$, varies somewhat from $\rho_P$.

The theoretical foundation for expressing $\rho_H$ as a function of $\rho_p$, f, H, and $\rho_{RBC}$ was also reported by Fricke in "A Mathematical Treatment of the Electric Conductivity and Capacity of Disperse Systems," The Physical Rev., Vol. 24, 2nd Series, July–December, 1924, which we have extracted to give:

$$(\rho_H/\rho_p) = \{1 + [((af(e^{-bx}-c))/(1-x))-1]H\}/\{1 + [((af(e^{-bx}-c))x/(1-x))-1]H\} \quad (9)$$

where x is the red blood cell to plasma conductivity ratio, and a, b, and c are constants derived from the curves of FIG. 3 of Fricke, in which a=1.56, b=1.02, and c=0.36 (to conform with Geddes and Sadler, f is used in place of the value of $-\beta(x)$ for x=0). Note that equation (9) reduces to equation (8) for x=0, and reduces to unity as x approaches 1. It should also be noted that equation (9) applies at any frequency for which the value of x (the definition now includes the influence of the membrane on red blood cell conductivity) can be measured.

The $\rho_L/\rho_H$ ratio can now be determined by dividing equation (8) by equation (9), which gives:

$$(\rho_L/\rho_H) = [(1+(f-1)H)/(1-H)]\{1+[((af(e^{-bx}-c))x/(1-x))-1]H\}/\{1+[((af(e^{-bx}-c))/(1-x))-1]H\} \quad (10)$$

Figure 18:
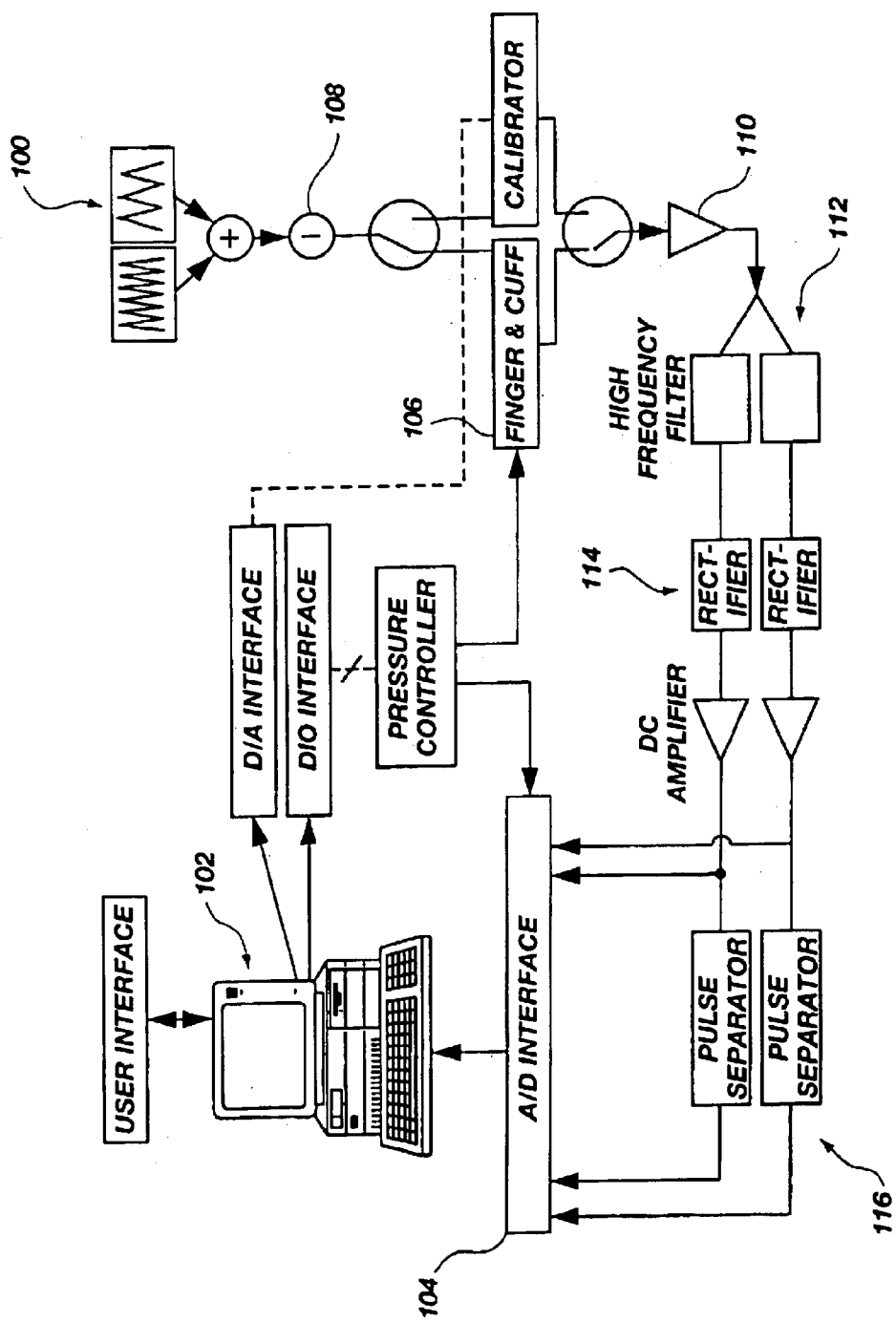
FIG. 18 is a block diagram of another hematocrit measurement system in accordance with this invention.

A block diagram of a two frequency embodiment of the system is shown in FIG. 18. Waveform generators 100 for both 100 KHz and 10 MHz frequencies are laboratory instruments, although of course these signals would typically be generated by internal oscillators in a hematocrit measurement instrument to be used in the field. An exemplary host computer 102 is a fully equipped IBM-compatible system running general-purpose laboratory data processing software, custom configured for the computations required for these studies. In the field, the host computer 102 would typically comprise a dedicated processor with dedicated software or firmware.

The computer 102 is equipped with a multi-channel analog-to-digital converter 104 for monitoring the physiological signals of a patient. A finger 106 or, alternatively, a calibration resistor string (for experimental purposes), is driven by a constant amplitude current source 108 at both the low and high frequencies. The mixed voltage is picked up by the inner electrode pair (see FIG. 17), amplified by a sensing amplifier 110, then separated by a complementary pair 112 of low-pass and high-pass filters into two signals. The separated signals at both frequencies are then rectified with rectifiers 114 to provide DC signals at the baseline levels with the pulses superimposed on these DC levels. The pulses are then separated from the baseline voltages by subtracting a low-pass filtered signal from the pulse-containing signal using pulse separators 116. These pulses are then amplified to a level where they can be visualized on an oscilloscope display on the computer 102. The computer 102 monitors four signals: the two baselines and the two pulses. From these signals, the hematocrit calculations are performed using the equations described above.

Automated Calibration

Figure 19:
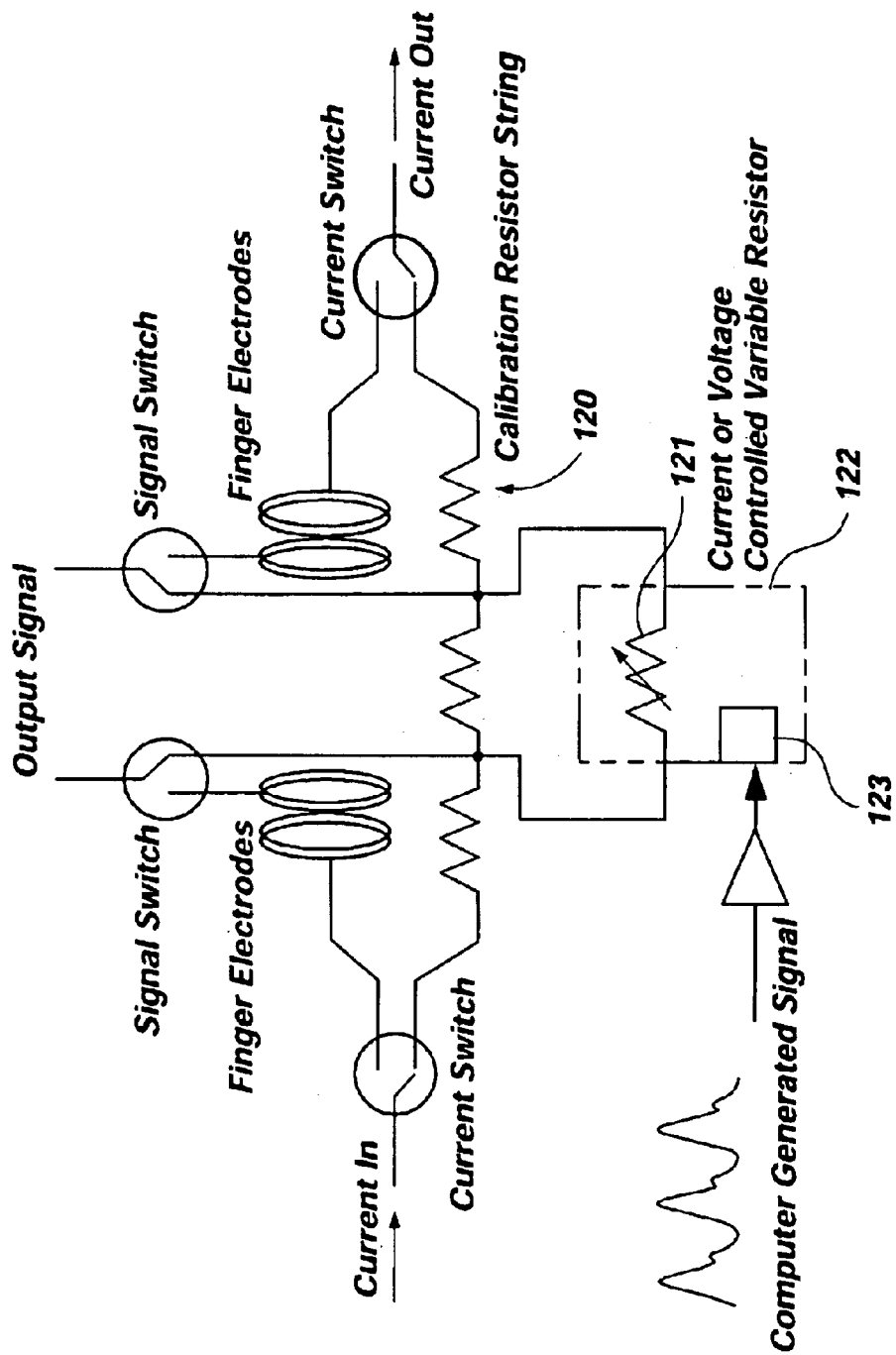
FIG. 19 is a diagram of a calibration system of the hematocrit measurement system of FIG. 18.

An automated calibration system can enhance the accuracy of the hematocrit H measurement by compensating for drift in the electronics, by periodically measuring the high and low frequency current ratios and the circuit gain ratios. To understand the calibration process, equation (7) is rewritten to give:

$$(\rho_L/\rho_H) = C' \cdot (\Delta \text{Volt}_H'/\Delta \text{Volt}_L')(\text{Volt}_L'^2/\text{Volt}_H'^2) \quad (11)$$

where the factor C' is an instrumentation calibration factor. The primes on the voltage parameters represent voltage measurements as opposed to true voltages existing at the measurement site. C', which includes the fixed current ratio $I_H/I_L$, and circuit gain ratios, then becomes:

$$C' = (I_H/I_L)(A_H/A_L)^2(DA_L/DA_H) \quad (12)$$

where $A_H$ and $A_L$ are the net amplification factors for the $V_H$ and $V_L$ channels, respectively; and $DA_H$ and $DA_L$ are the net pulse amplification factors for the respective frequencies. To the extent that the net amplification factors are linear (which include the sensing amplifier 110, filters 112, and rectifiers 114), the system can be calibrated by a single adjustment of the calibration factor C'. One method to obtain a value for C' uses a string of three resistors, connected either manually or by switching after the calibration is automated, in place of the finger. This puts the resistor string (shown as 120 in FIG. 19) in the circuit. The string of three resistors preferably approximates the resistance of a body part, such as a finger, at which hematocrit is to be measured. For example, the resistors may each have a resistance of about 500Ω or of about 560Ω.

Referring once again to FIG. 18, the constant amplitude current source 108 pushes the fixed currents at both frequencies through the resistor string 120 (of FIG. 19) and the sensing amplifier 110 receives the differential signal from the two ends of the center resistor. To produce a pulse analogous to the blood-caused impedance pulse in the finger, a fourth resistor 122 of FIG. 19, which is larger and variable, can be placed in parallel with the center resistor and varied by some means. One embodiment for the parallel resistor 122 is a semiconductor photoresistor 121 enclosed in an opaque cylinder, which also contains a light emitting diode 123. The current drive to the diode 123 will be varied in the shape of an arterial impedance pulse from a signal generated in the computer 102.

This configuration and method of pulse generation assures that both the base impedances and impedance pulses are of the same amplitude at both the high and low frequencies. Once equality of both base and pulse impedances is assured, it is possible to measure all the parameters of equation (11), on the same electronics that measure the finger parameters, with $(\rho_L/\rho_H)=1.0$, and solve for C' by:

$$C' = (\Delta \text{Volt}_L'/\Delta \text{Volt}_H')(\text{Volt}_H'^2/\text{Volt}_L'^2) \quad (13)$$

The reader should note that various mathematical terms (e.g., product and ratio) appear in some of the appended claims. The inventors have used the term "effective" in the claims in association with these mathematical terms to clarify the fact that this invention includes within its scope, among other things, all systems and methods by which hematocrit is calculated using the variables and constants as described herein. The invention is not limited to any particular system or method for correlating hematocrit to these variables and constants, nor is it limited to any particular order or form of calculation. In other words, the invention includes within its scope all systems and methods for calculating hematocrit from the variables and constants described herein which "effectively" calculate hematocrit in the manner described herein, no matter the actual method by which the calculation is performed. Also, it should be understood that the phrase "effectively determining a ratio," for example, is meant to include, not exclude, the act of actually determining the ratio.

Although this invention has been described with reference to particular embodiments, the invention is not limited to these described embodiments. For example, it should be understood that the signal enhancing effect described above as being associated with the application of pressure to the finger or other body part under test can be achieved in any of the embodiments disclosed herein. Thus, the invention is limited only by the appended claims, which include within their scope all equivalent devices and methods that operate according to the principles of the invention as described.

What is claimed is:

1. An assemblage for noninvasively measuring a patient's hematocrit, comprising:
    a first pair of electrodes configured to at least partially contact a body part of the patient at which hematocrit is to be measured, said first pair of electrodes being connectable to an electrical current source;
    a second pair of electrodes configured to at least partially contact the body part at which hematocrit is to be measured, said second pair of electrodes being connectable to an electrical impedance measurement apparatus; and
    a pressurization component comprising:
        an at least partially hollow, outer rigid member; and
        at least one inner pliable member disposed within said outer rigid member, said at least one inner pliable member being partially sealed against said outer rigid member to form a pressurization bladder between said outer rigid member and said at least one inner pliable member, said at least one inner pliable member including a receptacle including a closed end and being configured to receive at least a portion of a body part,
    said pressurization component being configured to apply pressure externally to said at least a portion of the body part, at least one electrode of said first and second pairs of electrodes being positionable between a portion of said pressurization component and said at least a portion of the body part.

2. The assemblage of claim 1, wherein said electrical impedance measurement apparatus is configured to measure electrical impedance of at least one frequency between electrodes of said second pair on the body part.

3. The assemblage of claim 1, wherein said pressurization component is associated with a pressure measurement apparatus configured to detect a change in pressure.

4. The assemblage of claim 3, wherein said pressure measurement apparatus is configured to detect a pulsatile change of pressure within said pressurization component.

5. The assemblage of claim 3, wherein said pressure measurement apparatus comprises a pressure cuff.

6. The assemblage of claim 1, wherein, upon introducing pressure into said pressurization bladder, said at least one inner pliable member applies pressure to at least a portion of a body part disposed within said receptacle.

7. The assemblage of claim 1, wherein at least one electrode of said first and second pairs of electrodes includes an elongate member configured to contact the body part.

8. The assemblage of claim 7, wherein at least one of said first and second pairs of electrodes further includes another elongate member configured to connect to said electrical current source.

9. The assemblage of claim 8, wherein said at least one electrode is substantially linear.

10. The assemblage of claim 8, wherein said at least one electrode is nonlinear.

11. The assemblage of claim 1, further comprising at least one connector configured to connect at least one electrode to external electronic componentry.

12. The assemblage of claim 11, wherein said at least one connector is configured to connect at least two electrodes to external electronic componentry.

13. The assemblage of claim 11, wherein said at least one connector is further configured to connect said pressurization component to a pressure supply and control apparatus.

14. The assemblage of claim 11, wherein said at least one connector is further configured to connect said pressurization component to a pressure source.

15. The assemblage of claim 1, wherein at least two electrodes of said first and second pairs of electrodes are positionable between said pressurization component and the body part.

16. The assemblage of claim 15, wherein said pressurization component is configured to apply a pressure externally to at least a portion of the body part.

17. The assemblage of claim 15, wherein at least a portion of said pressurization component is pliable.

18. The assemblage of claim 15, wherein said pressurization component carries at least a portion of at least one electrode of each of said first and second pairs of electrodes.

19. The assemblage of claim 15, wherein said pressurization component carries each electrode of each of said first and second pairs of electrodes.

20. The assemblage of claim 1, further comprising at least one retaining component configured to retain at least one electrode on the body part.

21. The assemblage of claim 20, wherein said at least one retaining component comprises at least one of adhesive material, a retaining sleeve configured to receive an end of said at least one electrode, a receptacle and electrode end configured to be interconnected, and a material that remains substantially deformed.

22. An assemblage for noninvasively measuring a patient's hematocrit, comprising:
    a first pair of elongate electrodes configured to at least partially contact a body part of the patient at which hematocrit is to be measured in mutually parallel relation to one another, said first pair of elongate electrodes being connectable to an electrical current source;
    a second pair of elongate electrodes configured to at least partially contact the body part at which hematocrit is to be measured in mutually parallel relation to one another, said second pair of elongate electrodes being connectable to an electrical impedance measurement apparatus; and
    at least one retention component on at least one elongate electrode of each of said first and second pairs of elongate electrodes with one of said first and second pairs of elongate electrodes being positioned between the other of said first and second pairs of elongate electrodes, said at least one retention component being configured to secure at least one elongate electrode to the body part and including a receptacle on said at least one elongate electrode and an end portion of said at least one elongate electrode being configured to interconnect with said receptacle, said end portion including:
        retaining regions, each retaining region having a retaining width that is greater than a receptacle width of said receptacle; and
        a constricted region located adjacent each retaining region, said constricted region having a constricted width that is at most about equal to said receptacle width.

23. The assemblage of claim 22, wherein said at least one retention component comprises a retaining sleeve on said at least one elongate electrode, said retaining sleeve configured to receive and hold an end of said at least one elongate electrode.

24. The assemblage of claim 22, further comprising a pressurization component.

* * * * *